United States Patent
Wonneberger et al.

(10) Patent No.: US 9,630,973 B2
(45) Date of Patent: Apr. 25, 2017

(54) DOUBLE DONOR FUNCTIONALISATION OF THE PERI-POSITIONS OF PERYLENE AND NAPHTHALENE MONOIMIDE VIA VERSATILE BUILDING BLOCKS

(71) Applicants: BASF SE, Ludwigshafen (DE); MAX-PLANCK-GESELLSCHAFT ZUR FOERDERUNG DER WISSENSCHAFTEN E.V., Munich (DE)

(72) Inventors: Henrike Wonneberger, Mannheim (DE); Helmut Reichelt, Neustadt (DE); Yulian Zagranyarski, Sofia (BG); Chen Li, Cologne (DE); Klaus Muellen, Cologne (DE); Long Chen, Mainz (DE)

(73) Assignees: BASF SE, Ludwigshafen (DE); Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 0 days.

(21) Appl. No.: 14/422,254

(22) PCT Filed: Aug. 27, 2013

(86) PCT No.: PCT/IB2013/058005
§ 371 (c)(1),
(2) Date: Feb. 18, 2015

(87) PCT Pub. No.: WO2014/033620
PCT Pub. Date: Mar. 6, 2014

(65) Prior Publication Data
US 2015/0225413 A1 Aug. 13, 2015

Related U.S. Application Data

(60) Provisional application No. 61/694,782, filed on Aug. 30, 2012.

(30) Foreign Application Priority Data

Aug. 30, 2012 (EP) .................................... 12182324

(51) Int. Cl.
*C07D 471/06* (2006.01)
*C07D 491/06* (2006.01)
(Continued)

(52) U.S. Cl.
CPC ......... *C07D 491/06* (2013.01); *C07D 221/18* (2013.01); *C07D 239/70* (2013.01);
(Continued)

(58) Field of Classification Search
CPC .. C07D 471/06; C07D 491/06; C07D 239/70; C07D 221/18
(Continued)

(56) References Cited

U.S. PATENT DOCUMENTS 3,163,659 A 12/1964 Sieber
4,207,255 A 6/1980 Eisfeld et al.
(Continued)

FOREIGN PATENT DOCUMENTS

CN 1681792 A 10/2005
CN 101351524 A 1/2009
(Continued)

OTHER PUBLICATIONS

Nagao et al., Synthesis and Properties of Dicarboximide Derivatives of Perylene and Azaperylene, Heterocycles, vol. 80, No. 2, pp. 1197-1213 (2010).*
(Continued)

*Primary Examiner* — Deepak Rao
(74) *Attorney, Agent, or Firm* — Oblon, McClelland, Maier & Neustadt, L.L.P.

(57) ABSTRACT

The present invention provides the compounds of formulae (3) and (1) wherein n is 0 or 1, $R^{13}$ and $R^{14}$ are the same or different and are selected from the group consisting of $NHR^{310}$, $NR^{311}R^{312}$, $OR^{313}$, $SR^{314}$ and $R^{315}$, or $R^{13}$ and $R^{14}$ together are selected from the group consisting of (a), (b) and (c), and X is Cl, Br of I, and a process for the preparation of compounds of formula (3) comprising the compounds of formula (1) as key intermediates.

(Continued)

-continued

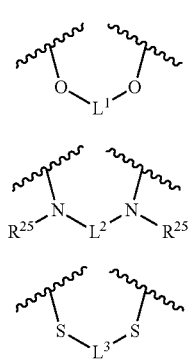

18 Claims, 4 Drawing Sheets

(51) Int. Cl.
| | |
|---|---|
| C07D 311/78 | (2006.01) |
| C07D 221/18 | (2006.01) |
| H01G 9/20 | (2006.01) |
| H01L 51/00 | (2006.01) |
| C07D 239/70 | (2006.01) |
| C07D 311/92 | (2006.01) |
| C09B 5/62 | (2006.01) |
| C09B 57/08 | (2006.01) |

(52) U.S. Cl.
CPC .......... *C07D 311/78* (2013.01); *C07D 311/92* (2013.01); *C07D 471/06* (2013.01); *C09B 5/62* (2013.01); *C09B 57/08* (2013.01); *H01G 9/2059* (2013.01); *H01L 51/0053* (2013.01); *H01L 51/0061* (2013.01); *H01G 9/2031* (2013.01); *Y02B 10/10* (2013.01); *Y02E 10/542* (2013.01)

(58) Field of Classification Search
USPC ............................................ 544/245; 546/39
See application file for complete search history.

(56) References Cited

U.S. PATENT DOCUMENTS

| | | | |
|---|---|---|---|
| 4,220,777 | A | 9/1980 | Karg et al. |
| 4,286,040 | A | 8/1981 | Van Lomm |
| 8,062,819 | B2 | 11/2011 | Yasukawa et al. |
| 2008/0261141 | A1 | 10/2008 | Yasukawa et al. |
| 2008/0269482 | A1 | 10/2008 | Pschirer et al. |
| 2015/0333275 | A1 | 11/2015 | Wonneberger et al. |

FOREIGN PATENT DOCUMENTS

| | | |
|---|---|---|
| CN | 101809116 A | 8/2010 |
| CN | 104418856 A | 3/2015 |
| DE | 1 154 799 B | 9/1963 |
| DE | 24 30 566 A1 | 1/1976 |
| DE | 25 20 642 A1 | 11/1976 |
| JP | 47-8465 B | 3/1972 |
| JP | 47-8466 B | 3/1972 |
| JP | 47-23706 B | 7/1972 |
| JP | 49-006527 B | 2/1974 |
| JP | 52-130820 A | 11/1977 |
| JP | 52-130822 A | 11/1977 |

OTHER PUBLICATIONS

Combined Office Action and Search Report issued Oct. 12, 2015 in Chinese Patent Application No. 201380045301.X (with English language translation and English translation of Categories of Cited Documents).
CA, No. 83:61699, RN No. 37898-84-3, 37860-87-0, 35652-30-3, Dec. 31, 1975, 21 Pages.
CA, No. 78:59793, RN No. 25507-27-1, 40847-93-6, 40847-92-5, 40847-91-4, 40847-61-8,40847-59-4,40847-58-3, 36026-56-9, 35955-74-9, Dec. 31, 1973, 21 Pages.
International Search Report issued Feb. 27, 2014 in PCT/IB2013/058005.
V.F. Anikin, et al., "Specific Features of Aminolysis of 4,5-Dichloronaphthalic Anhydride with Primary Amino Compounds", Russian Journal of Organic Chemistry, vol. 36, No. 11, (2000), pp. 1671-1676.
Zhe Sun, et al., "Soluble and Stable Heptazethrenebis(dicarboximide) with a Singlet Open-Shell Ground State", Journal of the American Society, vol. 133, No. 31, (2011), pp. 11896-11899.
J. Burdon, et al., "Polycyclic Fluoroaromatic Compounds-IV Some Reactions of Octafluoroacenaphthylene", Tetrahedron, vol. 21, No. 5, (1965), pp. 927-936.
Yulian Zagranyarski, et al., "Facile Transformation of Perylene Tetracarboxylic Acid Dianhydride into Strong Donor-Acceptor Chromophores", Organic Letters, vol. 14, No. 21, XP 55047589, (2012), pp. 5444-5447.
Yukinori Nagao, et al., "Synthesis and Properties of Dicarboximide Derivatives of Perylene and Azaperylene", Heterocycles, vol. 80, No. 2, (2010), pp. 1197-1213.
Ashok Keerthi, et al., "Synthesis of Perylene Dyes with Multiple Triphenylamine Substituents", Chemistry European Journal, vol. 18, No. 37, XP 55047505,(2012), pp. 11669-11676.
Supplementary Partial European Search Report issued on Mar. 24, 2016 in Patent Application No. EP 13 83 2040.
Combined Chinese Office Action and Search Report issued on Apr. 19, 2016 in Patent Application No. 201380045301.X (with partial English language translation and English language translation of categories of cited documents).
English language translation of the Office Action issued on Feb. 29, 2016 in Japanese Patent Application No. 2015-529174.
Extended European Search Report issued on Jun. 28, 2016 in Patent Application No. 13832040.3.
Xiaomei Huang, "Novel dyes based on naphthalimide moiety as electron acceptor for efficient dye-sensitized solar cells", Dyes and Pigments, vol. 90, XP028169793, 2011, pp. 297-303.
A. P Karishin, et al., "Synthesis of 5-chloro-6-iodoacenaphthene and its oxidation products", Zhurnal Obshchei Khimii, vol. 34, No. 3, XP002697940, 1964, p. 1.
A. P Karishin, et al., "Synthesis of 5, 6-diiodoacenaphthene and its oxidation products", Zhurnal Obshchei Khimii, vol. 34, No. 3, XP002697941, 1964, p. 1.
Patricia A. Blair, et al., "Photolytic, Thermal, Addition, and Cycloaddition Reactions of 2-Diazo-5,6- and -3,8-disubstituted Acenaphthenones", Journal of Organic Chemistry, vol. 69, No. 21, XP055064702, 2004, pp. 7123-7133.
Lihua Jia, et al "A novel chromatism switcher with double receptors selectively for Ag+ in neutral aqueous solution: 4,5-diaminoalkeneamino-*N*-alkyl-I,8-naphthalimides", Tetrahedron Letters, vol. 45, XP026080648, 2004, pp. 3969-3973.
Zhaochao Xu, et al., "Colorimetric and Ratiometric Fluorescent Chemosensor with a Large Red-Shift in Emission: Cu(II)-Only Sensing by Deprotonation of Secondary Amines as Receptor Conjugated to Naphthalimide Fluorophore", Organic Letters, vol. 7, No. 14, XP055064736, 2005, pp. 3029-3032.

* cited by examiner

DOUBLE DONOR FUNCTIONALISATION OF THE PERI-POSITIONS OF PERYLENE AND NAPHTHALENE MONOIMIDE VIA VERSATILE BUILDING BLOCKS

CROSS REFERENCE TO RELATED APPLICATION

This application is a 371 of PCT/IB2013/058005, filed on Aug. 27, 2013, which claims the benefit of U.S. Provisional Application No. 61/694,782, filed on Aug. 30, 2012, and claims priority to European Patent Application No. 12182324.9, filed on Aug. 30, 2012.

The present invention relates to naphthalene and perylene derivatives.

Many naphthalene and perylene derivates are important colorants. Beside this traditional application, naphthalene and, in particular, perylene derivatives gain more and more interest in other applications such as in organic field-effect transistors, organic light emitting devices, photovoltaic devices such as dye-sensitized solar cells (DSCs), and xerography.

The design and preparation of naphthalene and perylene derivatives, which are tuned to be suitable for a particular application, are an active area of research.

Not many processes are known for the preparation of perylene derivatives, which have electron-pulling groups such as an imide-group or anhydride group in the 3,4-positions and electron pushing groups such as aryl groups in 9,10 positions.

For example, Keerthi, A.; Liu, Y.; Wang, Q.; Valiyaveettil, S. *Chem. Eur. J.* 2012, 00 describes a process for the preparation of perylene derivatives, which have an imide or anhydride group in the 3,4-positions and substituted aryl groups in the 9,10 positions. The process is disadvantageous in that it involves a bromination step which yields a mixture of three brominated perylene derivatives, and thus the process also requires a separation step in order to obtain pure perylene derivatives. In addition, the bromination in the 9 and 10 positions is also accompanied by bromination in the 1 position, respectively, the 1 and 6 positions. Thus, the process does not offer a selective bromination in the 9 and 10 positions.

DE 1 154 799 describes the following process for the preparation of naphthalene derivatives, which have an anhydride group in the 1,8-position and Br or Cl in the 4,5-positions.

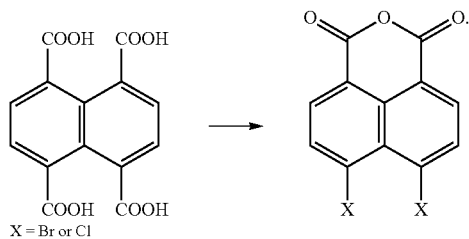
X = Br or Cl

The further substitution of the Br or Cl in 4,5-positions with electron-pushing groups is not described.

It was the object of the present invention to provide naphthalene and perylene derivatives, which are substituted in all four peri positions. It was a further object of the present invention to provide naphthalene derivatives, which have electron-pulling groups in the 1,8-positions and electron pushing groups in the 4,5 positions, and perylene derivatives which have electron-pulling groups in the 3,4-positions and electron pushing groups in the 9,10 positions.

This object is solved by the process of claim 1, the compounds of claim 11 and the compounds of claim 16.

The process of the present invention for the preparation of compounds of formula

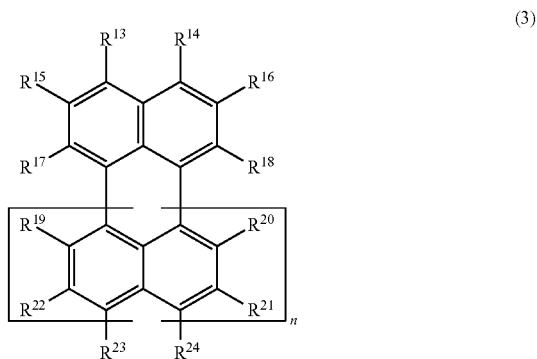

(3)

wherein
n is 0 or 1,
$R^{13}$ and $R^{14}$ are the same or different and are selected from the group consisting of $NHR^{310}$, $NR^{311}R^{312}$, $OR^{313}$, $SR^{314}$ and $R^{315}$,
wherein
$R^{310}$, $R^{311}$, $R^{312}$, $R^{313}$, $R^{314}$ and $R^{315}$ are $C_{1-20}$-alkyl, $C_{2-20}$-alkenyl, $C_{2-20}$-alkynl, $C_{5-8}$-cycloalkyl, $C_{6-14}$-aryl or heteroaryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3010}R^{3011}$, $O-R^{3012}$ and $S-R^{3013}$, and
$C_{6-14}$-aryl and heteroaryl may be substituted with one or more substituents selected from the group consisting of $C_{1-10}$-alkyl, $NR^{3014}R^{3015}$, $O-R^{3016}$ and $S-R^{3017}$,
wherein $R^{3010}$, $R^{3011}$, $R^{3012}$, $R^{3013}$, $R^{3014}$, $R^{3015}$, $R^{3016}$ and $R^{3017}$ are the same or different and are $C_{1-10}$-alkyl or phenyl,
or
$R^{13}$ and $R^{14}$ together are selected from the group consisting of

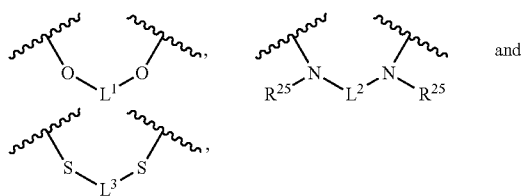

wherein
$L^1$ and $L^2$ are $C_{1-6}$-alkylene, $C_{6-14}$-arylene, or $C_{1-6}$-alkylene-$C_{6-14}$-arylene-$C_{1-6}$-alkylene,
$R^{25}$ is H, $C_{1-20}$-alkyl, $C_{2-20}$-alkenyl, $C_{2-20}$-alkynyl, $C_{5-8}$-cycloalkyl, $C_{6-14}$-aryl or heteroaryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3030}R^{3031}$, $O-R^{3032}$ and $S-R^{3033}$, and
$C_{6-14}$-aryl and heteroaryl may be substituted with one or more substituents selected from the group consisting of $C_{1-10}$-alkyl, $NR^{3034}R^{3035}$, $O-R^{3036}$ and $S-R^{3037}$,
wherein $R^{3030}$, $R^{3031}$, $R^{3032}$, $R^{3033}$, $R^{3034}$, $R^{3035}$, $R^{3036}$ and $R^{3037}$ are the same or different and are $C_{1-10}$-alkyl or phenyl, $L^3$ is a direct bond, $C_{1-6}$-alkylene, $C_{6-14}$-arylene, or $C_{1-6}$-alkylene-$C_{6-14}$-arylene-$C_{1-6}$-alkylene, $R^{15}$, $R^{16}$, $R^{17}$, $R^{18}$, $R^{19}$, $R^{20}$, $R^{21}$ and $R^{22}$ are the same or different and are selected from the group consisting of H, F, Cl, Br, I, CN, $R^{300}$, $OR^{301}$, $SR^{302}$, $OC(O)R^{303}$, $C(O)OR^{304}$ and $NR^{305}R^{306}$,
wherein $R^{300}$, $R^{301}$, $R^{302}$, $R^{303}$, $R^{304}$, $R^{305}$ and $R^{306}$ are $C_{1-20}$-alkyl, $C_{2-20}$-alkenyl, $C_{2-20}$-alkynyl, $C_{5-8}$-cycloalkyl, $C_{6-14}$-aryl or heteroaryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3000}R^{3001}$, $O-R^{3002}$, $S-R^{3003}$, $NO_2$, CN and halogen, and
$C_{6-14}$-aryl and heteroaryl may be substituted with one or more substituents selected from the group consisting of $C_{1-10}$-alkyl, $NR^{3004}R^{3005}$, $O-R^{3006}$, $S-R^{3007}$, $NO_2$, CN and halogen,
wherein $R^{3000}$, $R^{3001}$, $R^{3002}$, $R^{3003}$, $R^{3004}$, $R^{3005}$, $R^{3006}$ and $R^{3007}$ are the same or different and are $C_{1-10}$-alkyl or phenyl, or $R^{17}$ and $R^{19}$, respectively, $R^{18}$ and $R^{20}$ together are

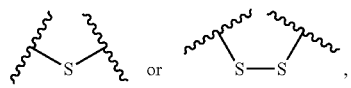

and
$R^{23}$ and $R^{24}$ together are

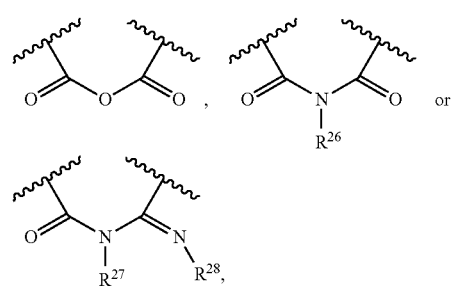

wherein
$R^{26}$, $R^{27}$ and $R^{28}$ are H, $C_{1-20}$-alkyl, $C_{2-20}$-alkenyl, $C_{2-20}$-alkynyl, $C_{5-8}$-cycloalkyl, $C_{6-14}$-aryl or heteroaryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $COOM^1$, $SO_3M^1$, $PO_3M^1$, $NO_2$, CN and halogen, and
$C_{6-14}$-aryl or heteroaryl may be substituted with one or more substituents selected from the group consisting of $C_{1-10}$-alkyl, $COOM^1$, $SO_3M^1$, $PO_3M^1$, $NO_2$, CN and halogen, wherein $M^1$ is H, alkali metal or $N(R^{3020}R^{3021}R^{3022}R^{3023})$,
wherein $R^{3020}$, $R^{3021}$, $R^{3022}$, and $R^{3023}$ are the same or different and are $C_{1-10}$-alkyl, or
$R^{27}$ and $R^{28}$ together with the unit

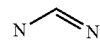

form a five or six membered ring which may be substituted with one or more substituents selected from the group consisting of $COOM^2$, $SO_3M^2$, $PO_3M^2$, $NO_2$, CN and halogen,
wherein $M^2$ is H, alkali metal or $N(R^{3024}R^{3025}R^{3026}R^{3027})$,
wherein $R^{3024}$, $R^{3025}$, $R^{3026}$, and $R^{3027}$ are the same or different and are $C_{1-10}$-alkyl,
comprises the step of treating a compound of formula

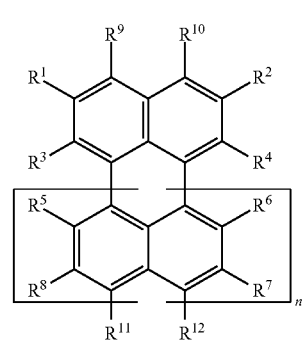

(2)

wherein
n is 0 or 1,
$R^9$ and $R^{10}$ are the same or different and are COOH or $COOR^{29}$,
wherein $R^{29}$ is $C_{1-20}$-alkyl, $C_{2-20}$-alkenyl, $C_{2-20}$-alkynyl, $C_{5-8}$-cycloalkyl, $C_{6-14}$-aryl or heteroaryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{2010}R^{2011}$, $O-R^{2012}$ and $S-R^{2013}$, and
$C_{6-14}$-aryl and heteroaryl may be substituted with one or more substituents selected from the group consisting of $C_{1-10}$-alkyl, $NR^{2014}R^{2015}$, $O-R^{2016}$ and $S-R^{2017}$,
wherein $R^{2010}$, $R^{2011}$, $R^{2012}$ and $R^{2013}$, $R^{2014}$, $R^{2015}$, $R^{2016}$ and $R^{2017}$ are the same or different and are $C_{1-10}$-alkyl or phenyl, or
$R^9$ and $R^{10}$ together are

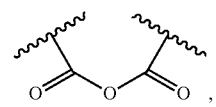 [SMILES: *C(=O)OC(*)=O]

$R^1$, $R^2$, $R^3$, $R^4$, $R^5$, $R^6$, $R^7$ and $R^8$ are the same or different and are selected from the group consisting of H, F, Cl, Br, I, CN, $R^{200}$, $OR^{201}$, $SR^{202}$, $OC(O)R^{203}$, $C(O)OR^{204}$ and $NR^{205}R^{206}$, wherein $R^{200}$, $R^{201}$, $R^{202}$, $R^{203}$, $R^{204}$, $R^{205}$ and $R^{206}$ are $C_{1-20}$-alkyl, $C_{2-20}$-alkenyl, $C_{2-20}$-alkynyl, $C_{5-8}$-cycloalkyl, $C_{6-14}$-aryl or heteroaryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{2000}R^{2001}$, $O-R^{2002}$, $S-R^{2003}$, $NO_2$, $CN$ and halogen, and $C_{6-14}$-aryl and heteroaryl may be substituted with one or more substituents selected from the group consisting of $C_{1-10}$-alkyl, $NR^{2004}R^{2005}$, $O-R^{2006}$, $S-R^{2007}$, $NO_2$, $CN$ and halogen, wherein $R^{2000}$, $R^{2001}$, $R^{2002}$, $R^{2003}$, $R^{2004}$, $R^{2005}$, $R^{2006}$ and $R^{2007}$ are the same or different and are $C_{1-10}$-alkyl or phenyl, or $R^3$ and $R^5$, respectively, $R^4$ and $R^6$ together are

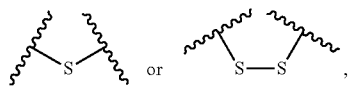

and $R^{11}$ and $R^{12}$ together are

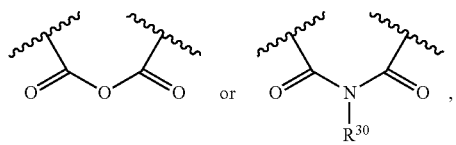

wherein $R^{30}$ is $C_{1-20}$-alkyl, $C_{2-20}$-alkenyl, $C_{2-20}$-alkynyl, $C_{5-8}$-cycloalkyl, $C_{6-14}$-aryl or heteroaryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NO_2$, $CN$ and halogen, and $C_{6-14}$-aryl and heteroaryl may be substituted with one or more substituents selected from the group consisting of $C_{1-10}$-alkyl, $NO_2$, $CN$ and halogen, with a) $M^3OH$, wherein $M^3$ is an alkali metal, $N(R^{400}R^{401}R^{402}R^{403})$, $P(R^{400}R^{401}R^{402}R^{403})$ or guanidinium, wherein $R^{400}$, $R^{401}$, $R^{402}$ and $R^{403}$ are the same or different and are selected from the group consisting of H, $C_{1-20}$-alkyl and $C_{6-14}$-aryl, wherein $C_{1-20}$-alkyl may be substituted with phenyl, and $C_{6-14}$-aryl may be substituted with $C_{1-10}$-alkyl, b) an acid and c) an X-donor, wherein X is Cl, Br or I, in order to obtain a compound of formula

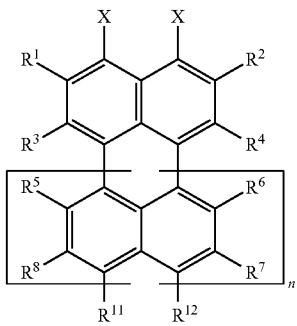

wherein

X is Cl, Br or I, n is 0 or 1, $R^1$, $R^2$, $R^3$, $R^4$, $R^5$, $R^6$, $R^7$ and $R^8$ are the same or different and are selected from the group consisting of H, F, Cl, Br, I, CN, $R^{200}$, $OR^{201}$, $SR^{202}$, $OC(O)R^{203}$, $C(O)OR^{204}$ and $NR^{205}R^{206}$, wherein $R^{200}$, $R^{201}$, $R^{202}$, $R^{203}$, $R^{204}$, $R^{205}$ and $R^{206}$ are $C_{1-20}$-alkyl, $C_{2-20}$-alkenyl, $C_{2-20}$-alkynyl, $C_{5-8}$-cycloalkyl, $C_{6-14}$-aryl or heteroaryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{2000}R^{2001}$, $O-R^{2002}$, $S-R^{2003}$, $NO_2$, $CN$ and halogen, and $C_{6-14}$-aryl and heteroaryl may be substituted with one or more substituents selected from the group consisting of $C_{1-10}$-alkyl, $NR^{2004}R^{2005}$, $O-R^{2006}$, $S-R^{2007}$, $NO_2$, $CN$ and halogen, wherein $R^{2000}$, $R^{2001}$, $R^{2002}$, $R^{2003}$, $R^{2004}$, $R^{2005}$, $R^{2006}$ and $R^{2007}$ are the same or different and are $C_{1-10}$-alkyl or phenyl, or $R^3$ and $R^5$, respectively, $R^4$ and $R^6$ together are

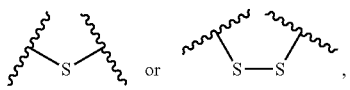

and $R^{11}$ and $R^{12}$ together are

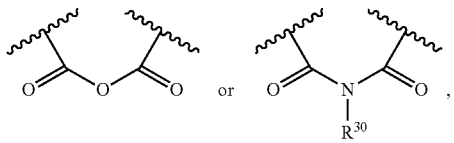

wherein $R^{30}$ is H, $C_{1-20}$-alkyl, $C_{2-20}$-alkenyl, $C_{2-20}$-alkynyl, $C_{5-8}$-cycloalkyl, $C_{6-14}$-aryl or heteroaryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NO_2$, $CN$ and halogen, and $C_{6-14}$-aryl and heteroaryl may be substituted with one or more substituents selected from the group consisting of $C_{1-10}$-alkyl, $NO_2$, $CN$ and halogen.

$C_{1-10}$-alkyl and $C_{1-20}$-alkyl can be branched or unbranched. Examples of $C_{1-10}$-alkyl are methyl, ethyl, butyl, iso-butyl, sec-butyl, tert-butyl, pentyl, isopentyl, hexyl, heptyl, octyl, 1,1-dimethyl-3,3-dimethylbutyl, nonyl and decyl. Examples of $C_{1-20}$-alkyl are $C_{1-10}$-alkyl, undecyl, dodecyl, tridecyl, tetradecyl, pentadecyl, hexadecyl, heptadecyl, octadecyl, nonadecyl and eicosyl, $C_{2-20}$-alkenyl can be branched or unbranched. Examples of $C_{2-20}$-alkenyl are vinyl, propenyl, cis-2-butenyl, trans-2-butenyl, 3-butenyl, cis-2-pentenyl, trans-2-pentenyl, cis-3-pentenyl, trans-3-pentenyl, 4-pentenyl, 2-methyl-3-butenyl, hexenyl, heptenyl, octenyl, nonenyl and docenyl, linoleyl ($C_{18}$), linolenyl ($C_{18}$), oleyl ($C_{18}$) and arachidonyl ($C_{20}$).

$C_{2-20}$-alkynyl can be branched or unbranched. Examples of $C_{2-20}$-alkynyl are ethynyl, 2-propynyl, 2-butynyl, 3-butynyl, pentynyl, hexynyl, heptynyl, octynyl, nonynyl, decynyl, undecynyl, dodecynyl, undecynyl, dodecynyl, tridecynyl, tetradecynyl, pentadecynyl, hexadecynyl, heptadecynyl, octadecynyl, nonadecynyl and icosynyl ($C_{20}$).

Examples of $C_{5-8}$-cycloalkyl are cyclopentyl, cyclohexyl, cycloheptyl and cyclooctyl.

Examples of $C_{6-14}$-aryl are phenyl and naphthyl.

Examples of heteroaryl are monocyclic 5 membered heteroaryl containing one heteroatom such as pyrrolyl, furyl and thiophenyl, monocyclic 5 membered heteroaryl containing two heteroatoms such as imidazolyl, pyrazolyl, oxazolyl, isoxazolyl, thiazolyl, isothiazolyl, monocyclic 5 membered heteroaryl containing three heteroatoms such as 1,2,3-triazolyl, 1,2,4-triazolyl and oxadiazolyl, monocyclic 5 membered heteroaryl containing four heteroatoms such as tetrazolyl, monocyclic 6 membered heteroaryl containing one heteroatom such as pyridyl, monocyclic 6 membered heteroaryl containing two heteroatoms such as pyrazinyl, pyrimidinyl and pyridazinyl, monocyclic 6 membered heteroaryl containing three heteroatoms such as 1,2,3-triazinyl, 1,2,4-triazinyl and 1,3,5-triazinyl, monocyclic 7 membered heteroaryl containing one heteroatom such as azepinyl, and monocyclic 7 membered heteroaryl containing two heteroatoms such as 1,2-diazepinyl. Preferably, heteroary is a 5 to 7 membered heteroaryl.

Examples of halogen are F, Cl, Br and I.

Examples of $C_{1-6}$-alkylene are methylene, ethylene, propylene and butylene.

Examples of $C_{6-14}$-arylene are phenylene and naphthalene.

Examples of alkali metals are Na, K and Li.

Examples of $N(R^{400}R^{401}R^{402}R^{403})$ are tetra(n-butyl)ammonium and decyl-methyl-dioctylammonium.

Examples of hexa($C_{1-10}$-alkyl)-guanidinium are hexamethylguanidinium and hexaethylguanidinium.

Examples of acids are Brönsted-acids such as HCl, $H_2SO_4$ and acetic acid.

Examples of X-donors are X—X, X-succinimide and N,N'-di-X-isocyanuric acid.

Preferably, $R^{13}$ and $R^{14}$ are the same and are selected from the group consisting of $NHR^{310}$, $NR^{311}R^{312}$ and $R^{315}$,
wherein
$R^{310}$, $R^{311}$, $R^{312}$ and $R^{315}$ are $C_{1-20}$-alkyl, $C_{2-20}$-alkenyl, $C_{2-20}$-alkynyl, $C_{5-8}$-cycloalkyl, $C_{6-14}$-aryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3010}R^{3011}$, O—$R^{3012}$ and S—$R^{3013}$, and
$C_{6-14}$-aryl may be substituted with one or more substituents selected from the group consisting of $C_{1-10}$-alkyl, $NR^{3014}R^{3015}$, O—$R^{3016}$ and S—$R^{3017}$,
wherein $R^{3010}$, $R^{3011}$, $R^{3012}$, $R^{3013}$, $R^{3014}$, $R^{3015}$, $R^{3016}$ and $R^{3017}$ are the same or different and are $C_{1-10}$-alkyl or phenyl,
or
$R^{13}$ and $R^{14}$ together are

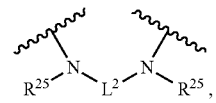

wherein
$L^2$ is $C_{1-6}$-alkylene, $C_{6-14}$-arylene, or $C_{1-6}$-alkylene-$C_{6-14}$-arylene-$C_{1-6}$-alkylene,
$R^{25}$ is H, $C_{1-20}$-alkyl, $C_{2-20}$-alkenyl, $C_{2-20}$-alkynyl, $C_{5-8}$-cycloalkyl, or $C_{6-14}$-aryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3030}R^{3031}$, O—$R^{3032}$ and S—$R^{3033}$, and
$C_{6-14}$-aryl may be substituted with one or more substituents selected from the group consisting of $C_{1-10}$-alkyl, $NR^{3034}R^{3035}$, O—$R^{3036}$ and S—$R^{3037}$,
wherein $R^{3030}$, $R^{3031}$, $R^{3032}$, $R^{3033}$, $R^{3034}$, $R^{3035}$, $R^{3036}$ and $R^{3037}$ are the same or different and are $C_{1-10}$-alkyl or phenyl.

More preferably, $R^{13}$ and $R^{14}$ are the same and are selected from the group consisting of $NHR^{310}$, $NR^{311}R^{312}$ and $R^{315}$,
wherein
$R^{310}$, $R^{311}$, $R^{312}$ and $R^{315}$ are $C_{6-14}$-aryl,
wherein
$C_{6-14}$-aryl may be substituted with one or more substituents selected from the group consisting of $C_{1-10}$-alkyl, $NR^{3014}R^{3015}$, O—$R^{3016}$ and S—$R^{3017}$,
wherein $R^{3010}$, $R^{3011}$, $R^{3012}$, $R^{3013}$, $R^{3014}$, $R^{3015}$, $R^{3016}$ and $R^{3017}$ are the same or different and are $C_{1-10}$-alkyl or phenyl,
or
$R^{13}$ and $R^{14}$ together are

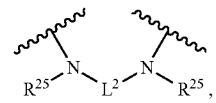

wherein
$L^2$ is $C_{1-6}$-alkylene, $C_{6-14}$-arylene, or $C_{1-6}$-alkylene-$C_{6-14}$-arylene-$C_{1-6}$-alkylene, $R^{25}$ is H, $C_{1-20}$-alkyl or $C_{6-14}$-aryl,
wherein
$C_{1-20}$-alkyl may be substituted with one or more substituents selected from the group consisting of phenyl, $NR^{3030}R^{3031}$, O—$R^{3032}$ and S—$R^{3033}$, and
$C_{6-14}$-aryl may be substituted with one or more substituents selected from the group consisting of $C_{1-10}$-alkyl, $NR^{3034}R^{3035}$, O—$R^{3036}$ and S—$R^{3837}$,
wherein $R^{3030}$, $R^{3031}$, $R^{3032}$, $R^{3033}$, $R^{3034}$, $R^{3035}$, $R^{3036}$ and $R^{3037}$ are the same or different and are $C_{1-10}$-alkyl or phenyl.

Most preferably, $R^{13}$ and $R^{14}$ are the same and are selected from the group consisting of $NHR^{310}$ and $R^{315}$, wherein
$R^{310}$ and $R^{315}$ are $C_{6-14}$-aryl,
wherein
$C_{6-14}$-aryl may be substituted with $NR^{3014}R^{3015}$, wherein $R^{3014}$ and $R^{3015}$ are phenyl,
or
$R^{13}$ and $R^{14}$ together are

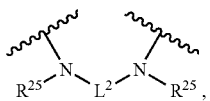

wherein
$L^2$ is $C_{1-6}$-alkylene or $C_{6-14}$-arylene,
$R^{25}$ is H or $C_{6-14}$-aryl.
Preferably, $R^{23}$ and $R^{24}$ together are

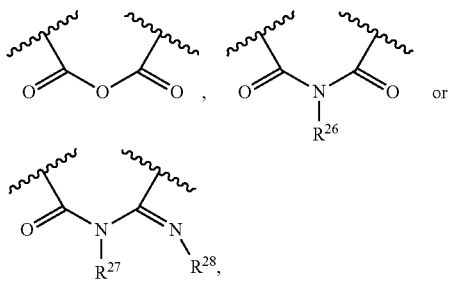

wherein
$R^{26}$, $R^{27}$ and $R^{28}$ are $C_{1-20}$-alkyl or $C_{6-14}$-aryl,
wherein
$C_{1-20}$-alkyl may be substituted with one or more substituents selected from the group consisting of phenyl, $COOM^1$, $SO_3M^1$, $PO_3M^1$, $NO_2$, CN and halogen, and
$C_{6-14}$-aryl may be substituted with one or more substituents selected from the group consisting of $C_{1-10}$-alkyl, $COOM^1$, $SO_3M^1$, $PO_3M^1$, $NO_2$, CN and halogen,
wherein $M^1$ is H, alkali metal or $N(R^{3020}R^{3021}R^{3022}R^{3023})$,
wherein $R^{3020}$, $R^{3021}$, $R^{3022}$, and $R^{3023}$ are the same or different and are $C_{1-10}$-alkyl,
or
$R^{27}$ and $R^{28}$ together with the unit

form a five or six membered ring which may be substituted with one or more substituents selected from the group consisting of $COOM^2$, $SO_3M^2$, $PO_3M^2$, $NO_2$, CN and halogen,
wherein $M^2$ is H, alkali metal or $N(R^{3024}R^{3025}R^{3026}R^{3027})$,
wherein $R^{3024}$, $R^{3025}$, $R^{3026}$, and $R^{3027}$ are the same or different and are $C_{1-10}$-alkyl.
More preferably, $R^{23}$ and $R^{24}$ together are

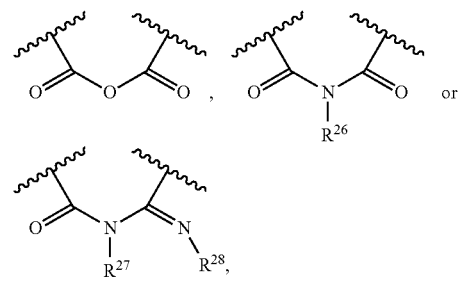

wherein
$R^{26}$, $R^{27}$ and $R^{28}$ are $C_{1-20}$-alkyl or $C_{6-14}$-aryl,
wherein
$C_{1-20}$-alkyl may be substituted with one or more substituents selected from the group consisting of phenyl and $COOM^1$, and
$C_{6-14}$-aryl may be substituted with one or more substituents selected from the group consisting of $C_{1-10}$-alkyl, $COOM^1$,
wherein $M^1$ is H, alkali metal or $N(R^{3020}R^{3021}R^{3022}R^{3023})$,
wherein $R^{3020}$, $R^{3021}$, $R^{3022}$, and $R^{3023}$ are the same or different and are $C_{1-10}$-alkyl,
or
$R^{27}$ and $R^{28}$ together with the unit

form a five or six membered ring which may be substituted with one or more substituents selected from the group consisting of $COOM^2$ and CN,
wherein $M^2$ is H, alkali metal or $N(R^{3024}R^{3025}R^{3026}R^{3027})$,
wherein $R^{3024}$, $R^{3025}$, $R^{3026}$, and $R^{3027}$ are the same or different and are $C_{1-10}$-alkyl.
Most preferably, $R^{23}$ and $R^{24}$ together are

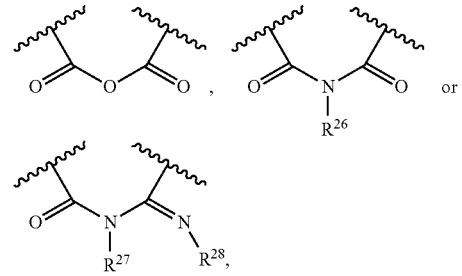

wherein
$R^{26}$, $R^{27}$ and $R^{28}$ are $C_{1-20}$-alkyl or $C_{6-14}$-aryl,
wherein
$C_{1-20}$-alkyl may be substituted with $COOM^1$,
wherein $M^1$ is H,
or
$R^{27}$ and $R^{28}$ together with the unit

form a five membered ring which may be substituted with one or more substituents selected from the group consisting of $COOM^2$ and CN, wherein $M^2$ is H.

Preferably, $R^{15}$, $R^{16}$, $R^{17}$, $R^{18}$, $R^{19}$, $R^{20}$, $R^{21}$ and $R^{22}$ are the same or different and are selected from the group consisting of H, Cl, Br, I and CN. More preferably, $R^{15}$, $R^{16}$, $R^{17}$, $R^{18}$, $R^{19}$, $R^{20}$, $R^{21}$ and $R^{22}$ are the same or different and are H or Cl.

Preferably, $R^1$, $R^2$, $R^3$, $R^4$, $R^5$, $R^6$, $R^7$ and $R^8$ are the same or different and are selected from the group consisting of H, Cl, Br, I and CN. More preferably, $R^1$, $R^2$, $R^3$, $R^4$, $R^5$, $R^6$, $R^7$ and $R^8$ are the same or different and are H or Cl.

Preferably, n is 1,

Preferably, if n=1, $R^{15}$, $R^{16}$, $R^{21}$ and $R^{22}$ are H, and $R^{17}$, $R^{18}$, $R^{19}$ and $R^{20}$ are the same or different and are selected from the group consisting of H, F, Cl, Br, I, CN, $R^{300}$, $OR^{301}$, $SR^{302}$, $OC(O)R^{303}$, $C(O)OR^{304}$ and $NR^{305}R^{306}$, wherein $R^{300}$, $R^{301}$, $R^{302}$, $R^{303}$, $R^{304}$, $R^{305}$ and $R^{306}$ are $C_{1-20}$-alkyl, $C_{2-20}$-alkenyl, $C_{2-20}$-alkynyl, $C_{5-8}$-cycloalkyl or $C_{6-14}$-aryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3000}R^{3001}$, O—$R^{3002}$, S—$R^{3003}$, $NO_2$, CN and halogen, and $C_{6-14}$-aryl may be substituted with one or more substituents selected from the group consisting of $C_{1-10}$-alkyl, $NR^{3004}R^{3005}$, O—$R^{3006}$, S—$R^{3007}$, $NO_2$, CN and halogen, wherein $R^{3000}$, $R^{3001}$, $R^{3002}$, $R^{3003}$, $R^{3004}$, $R^{3005}$, $R^{3006}$ and $R^{3007}$ are the same or different and are $C_{1-10}$-alkyl or phenyl, or $R^{17}$ and $R^{19}$, respectively, $R^{18}$ and $R^{20}$ together are

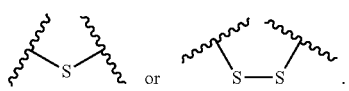

More preferably, if n=1, $R^{15}$, $R^{16}$, $R^{21}$ and $R^{22}$ are H, and $R^{17}$, $R^{18}$, $R^{19}$ and $R^{20}$ are the same or different and are selected from the group consisting of H, Cl, Br, I and CN.

Most preferably, if n=1, $R^{15}$, $R^{16}$, $R^{21}$ and $R^{22}$ are H, and $R^{17}$, $R^{18}$, $R^{19}$ and $R^{20}$ are the same or different and are H or Cl.

Preferably, if n is 1, $R^1$, $R^2$, $R^7$ and $R^8$ are H, and $R^3$, $R^4$, $R^5$ and $R^6$ are the same or different and are selected from the group consisting of H, F, Cl, Br, I, CN, $R^{200}$, $OR^{201}$, $SR^{202}$, $OC(O)R^{203}$, $C(O)OR^{204}$ and $NR^{205}R^{206}$, wherein $R^{200}$, $R^{201}$, $R^{202}$, $R^{203}$, $R^{204}$, $R^{205}$ and $R^{206}$ are $C_{1-20}$-alkyl, $C_{2-20}$-alkenyl, $C_{2-20}$-alkynyl, $C_{5-8}$-cycloalkyl or $C_{6-14}$-aryl, wherein $C_{1-20}$-alkyl, $C_{2-20}$-alkenyl, $C_{2-20}$-alkynyl and $C_{5-8}$-cycloalkyl may be substituted with $R^{2001}$, one or more substituents selected from the group consisting of phenyl, $NR^{2000}R^{2001}$, O—$R^{2002}$, S—$R^{2003}$, $NO_2$, CN and halogen, and $C_{6-14}$-aryl may be substituted with one or more substituents selected from the group consisting of $C_{1-10}$-alkyl, $NR^{21304}R^{2005}$, O—$R^{2006}$, S—$R^{2007}$, $NO_2$, CN and halogen, wherein $R^{2000}$, $R^{2001}$, $R^{2002}$, $R^{2003}$, $R^{2004}$, $R^{2005}$, $R^{2006}$ and $R^{2007}$ are the same or different and are $C_{1-10}$-alkyl or phenyl, or $R^3$ and $R^5$, respectively, $R^4$ and $R^6$ together are

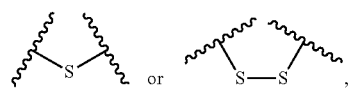

More preferably, if n is 1, $R^1$, $R^2$, $R^7$ and $R^8$ are H, and $R^3$, $R^4$, $R^5$ and $R^6$ are the same or different and are selected from the group consisting of H, Cl, Br, I and CN.

Most preferably, if n is 1, $R^1$, $R^2$, $R^7$ and $R^8$ are H, and $R^3$, $R^4$, $R^5$ and $R^6$ are H or Cl.

Preferably, $R^9$ and $R^{10}$ are the same and are COOH or $R^9$ and $R^{10}$ together are

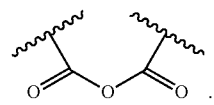 [SMILES: *C(=O)OC(*)=O]

More preferably, $R^9$ and $R^{10}$ together are

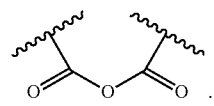 [SMILES: *C(=O)OC(*)=O]

Preferably, $R^{11}$ and $R^{12}$ together are

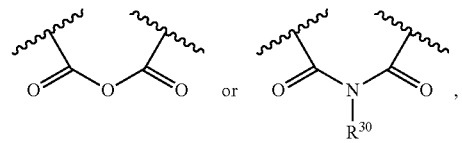

wherein $R^{30}$ is H, $C_{1-20}$-alkyl or $C_{6-14}$-aryl, wherein $C_{1-20}$-alkyl may be substituted with one or more substituents selected from the group consisting of phenyl, $NO_2$, CN and halogen, and $C_{6-14}$-aryl may be substituted with one or more substituents selected from the group consisting of $C_{1-10}$-alkyl, $NO_2$, CN and halogen.

More preferably, $R^{11}$ and $R^{12}$ together are

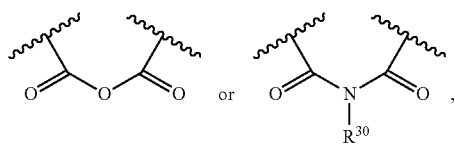

wherein $R^{30}$ is $C_{1-20}$-alkyl.

Most preferably, $R^{11}$ and $R^{12}$ together are

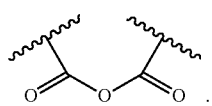

Preferably, X is Cl or Br, more preferably Br.

Preferably, the X-donor is X—X. More preferably, the X-donor is X—X, wherein X is Cl or Br. Most preferably, the X-donor is X—X, wherein X is Br.

Preferably, $M^3$ is an alkali metal, more preferably Na.

Preferably, the acid is a Brönsted-acid, more preferably it is acetic acid.

The compounds of formula (2) are commercially available or can be prepared by methods known in the art.

Preferably, the compound of formula (2) is first treated with $M^3OH$, followed by treatment with the acid and with the X-donor. However, it is possible to add the acid before the addition of the X-donor, simultaneously with the X-donor and/or after the addition of the X-donor. Usually the process is performed without the isolation of any intermediate products in a so-called "one pot reaction".

Preferably, the treatment with $M^3OH$, the treatment with the acid and the treatment with the X-donor are performed in an aqueous solvent such as water or mixtures of water with a suitable organic solvent such as tetrahydrofuran or dioxane. More preferably, the treatment with $M^3OH$, the treatment with the acid and the treatment with the X-donor are performed in water as solvent.

Preferably, the treatment with $M^3OH$ is performed at a temperature from 20 to 160° C., more preferably from 40 to 140° C., most preferably from 60 to 120° C.

Preferably, the molar ratio of $M^3OH$/compound of general formula (2) is 4/1 to 20/1, more preferably 4/1 to 10/1, most preferably 4/1 to 7/1.

If the acid is a one proton-donating Brönsted acid, preferably acetic acid, the preferred molar ratio of the acid/compound of general formula (2) is 4/1 to 10/1, more preferably 4/1 to 7/1.

Preferably, the treatment with the acid is performed at a temperature from 20 to 160° C., more preferably from 40 to 140° C., most preferably from 60 to 120° C.

Preferably, the molar ratio of the X-donor/compound of general formula (2) is 2/1 to 3/1, more preferably 2/1 to 2.8/1, most preferably 2.1/1 to 2.6/1.

Preferably, the treatment with the X-donor is performed at a temperature from 20 to 160° C., more preferably from 40 to 140° C., most preferably from 60 to 120° C.

The compound of formula (1) can be isolated by methods known in the art, for example by filtration.

The compounds of formula (3) can be directly obtained from the compounds of formula (1) or via intermediate compounds in multiple steps by methods known in the art.

For example, the compounds of formulae

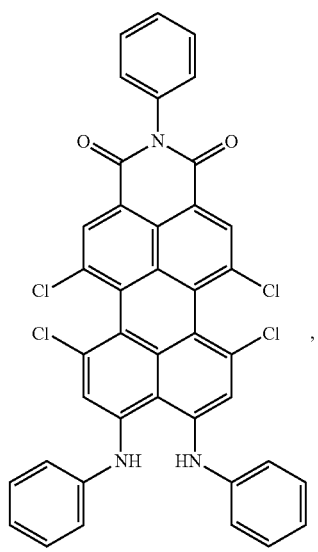

(3a)

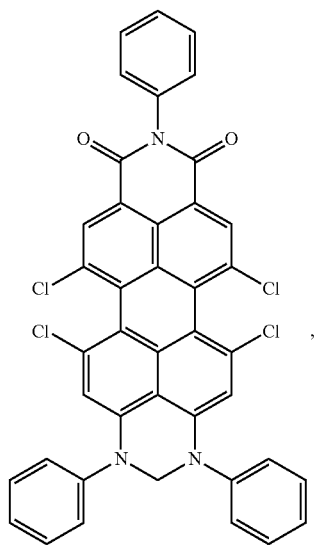

(3b)

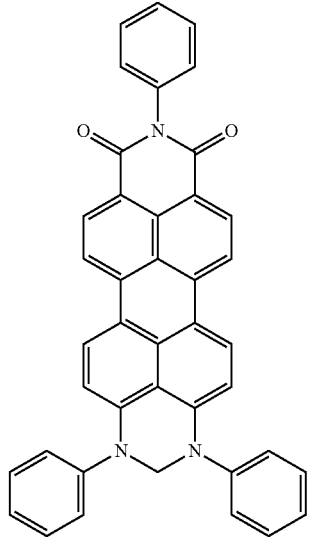

(3c)

-continued

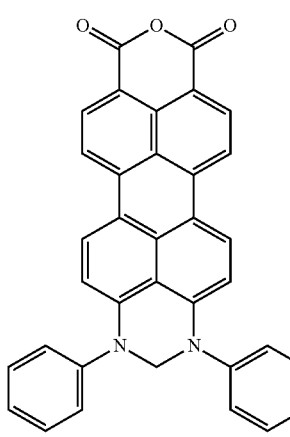

and

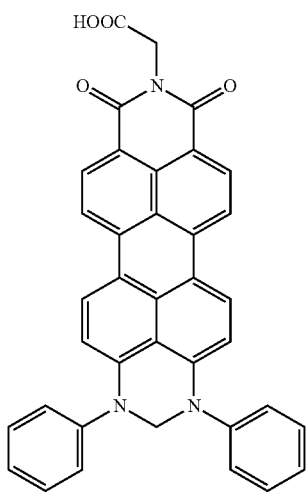

can be prepared from the compound of formula

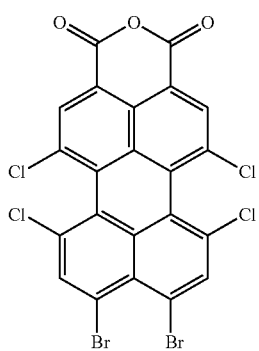

as follows:

The compound of formula (1a) can be reacted with aniline in order to obtain a compound of formula (3a), the compound of formula (3a) can be reacted with paraformaldehyde in order to obtain a compound of formula (3b), the compound of formula (3b) can be treated with potassium with potassium hydroxide in 1,2-ethanediol to obtain a compound of formula (3c), the compound of formula (3c) can be treated with potassium hydroxide in tert-butanol and 1,4-dioxane in order to obtain a compound of formula (3d), the compound of formula (3d) can be treated with glycine in the presence of imidazole in order to obtain a compound of formula (3e).

For example, the compound of formula

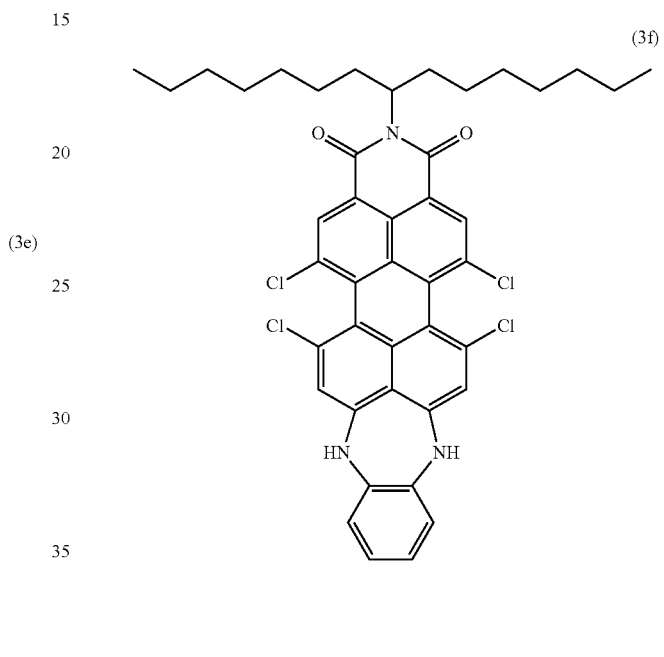

can be prepared from the compound of formula

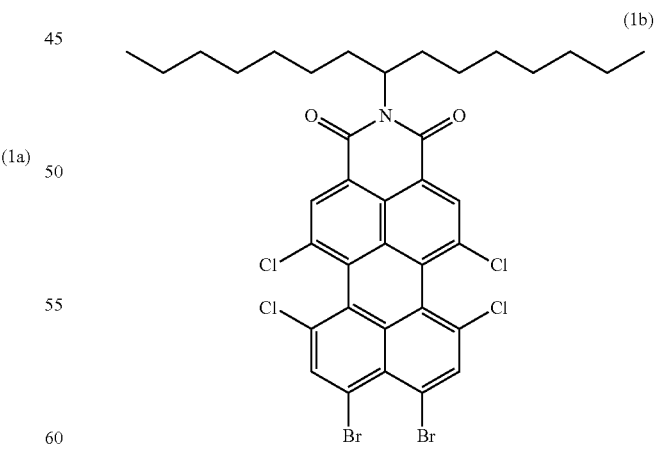

by treating the compound of formula (1 b) with 1,2-dioaminobenzene in order to obtain the compound of formula (3f).

For example the compounds of formulae

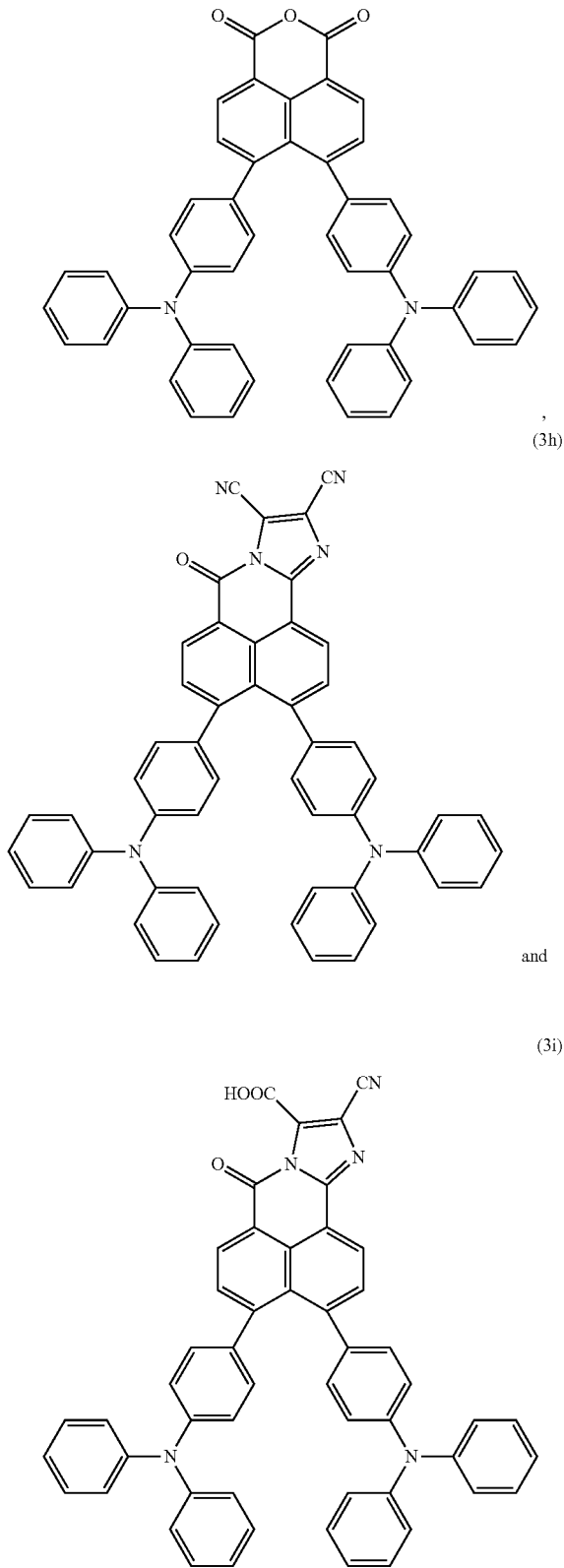

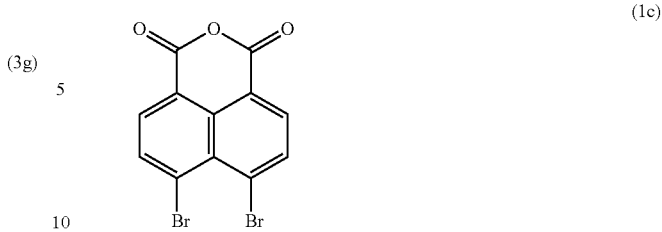

by the following process:

The compound of formula (1c) can be treated with 4-(diphenylamino)phenylboronic acid in the presence of Pd[P(Ph)$_3$]$_4$ in order to obtain the compound of formula (3g), the compound of formula (3g) can be reacted with 2,3-diaminomaleonitrile in order to obtain the compound of formula (3h), the compound of formula (3h) can be treated with sodium hydroxide in order to obtain the compound of formula (3i).

Also part of the invention are compounds of formula

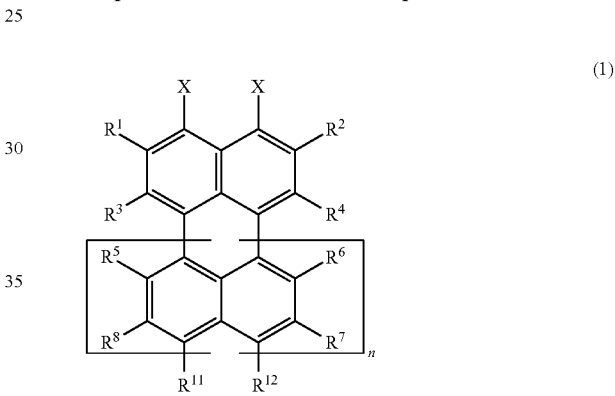

wherein
X is Cl, Br or I,
n is 0 or 1,
$R^1$, $R^2$, $R^3$, $R^4$, $R^5$, $R^6$, $R^7$ and $R^8$ are the same or different and are selected from the group consisting of H, F, Cl, Br, I, CN, $R^{200}$, $OR^{201}$, $SR^{202}$, $OC(O)R^{203}$, $C(O)OR^{264}$ and $NR^{205}R^{206}$,
wherein $R^{200}$, $R^{201}$, $R^{202}$, $R^{203}$, $R^{204}$, $R^{205}$ and $R^{206}$ are $C_{1-20}$-alkyl, $C_{2-20}$-alkenyl, $C_{2-20}$-alkynyl, $C_{5-8}$-cycloalkyl, $C_{6-14}$-aryl or heteroaryl,
wherein
$C_{1-20}$-alkyl, $C_{2-20}$-alkenyl, $C_{2-20}$-alkynyl and $C_{5-8}$-cycloalkyl may be substituted with $R^{2001}$, one or more substituents selected from the group consisting of phenyl, $NR^{2000}R^{2001}$, $O-R^{2002}$, $S-R^{2003}$, $NO_2$, CN and halogen, and
$C_{6-14}$-aryl and heteroaryl may be substituted with one or more substituents selected from the group consisting of $C_{1-10}$-alkyl, $NR^{2004}R^{2005}$, $O-R^{2006}$, $S-R^{2007}$, $NO_2$, CN and halogen,
wherein $R^{2000}$, $R^{2001}$, $R^{2002}$, $R^{2003}$, $R^{2004}$, $R^{2005}$, $R^{2006}$ and $R^{2007}$ are the same or different and are $C_{1-10}$-alkyl or phenyl, can be prepared from a compound of formula or
$R^3$ and $R^5$, respectively, $R^4$ and $R^6$ together are

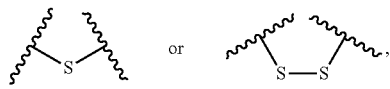

and
$R^{11}$ and $R^{12}$ together are

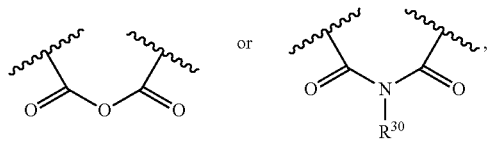

wherein $R^{30}$ is H, $C_{1-20}$-alkyl, $C_{2-20}$-alkenyl, $C_{2-20}$-alkynyl, $C_{5-8}$-cycloalkyl, $C_{6-14}$-aryl or heteroaryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NO_2$, CN and halogen, and
$C_{6-14}$-aryl and heteroaryl may be substituted with one or more substituents selected from the group consisting of $C_{1-10}$-alkyl, $NO_2$, CN and halogen,
with the proviso
that if n is 0, $R^1$, $R^2$, $R^3$ and $R^4$ are H, and X is Cl or Br, then $R^{11}$ and $R^{12}$ together are not

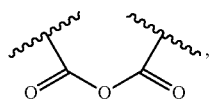 [SMILES: *C(=O)OC(*)=O]

that if n is 0, $R^1$, $R^2$, $R^3$ and $R^4$ are Br, and X is Br, then $R^{11}$ and $R^{12}$ together are not

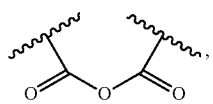 [SMILES: *C(=O)OC(*)=O]

and
that if n is 1, $R^1$, $R^2$, $R^3$, $R^4$, $R^7$ and $R^8$ are H, one of $R^5$ and $R^6$ is Br, and the other of $R^5$ and $R^6$ is H or Br, and X is Br, then $R^{11}$ and $R^{12}$ together are not

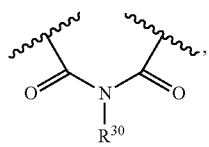

wherein $R^{30}$ is 2-ethylhexyl.
The preferences of n, $R^1$, $R^2$, $R^3$, $R^4$, $R^5$, $R^6$, $R^7$, $R^8$, $R^{11}$, $R^{12}$ and X given above for the process for the preparation of compounds of formula (3), also apply to the compounds of formula (1).

In particular preferred is the compound of formula

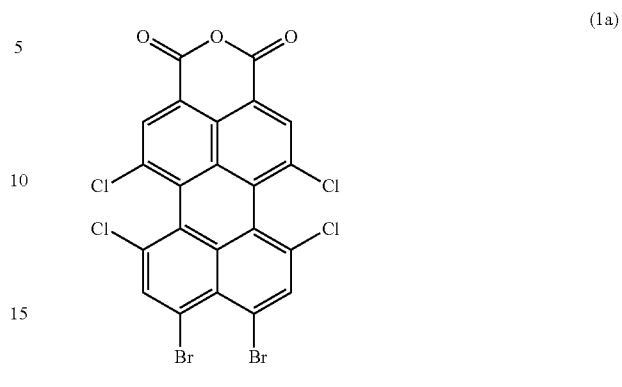

(1a)

The compounds of formula (1) are versatile building blocks.
Also part of the invention are compounds of formula

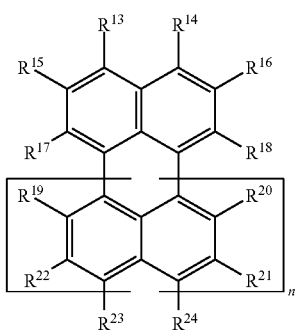

(3)

wherein
n is 0 or 1,
$R^{13}$ and $R^{14}$ are the same or different and are selected from the group consisting of $NHR^{310}$, $NR^{311}R^{312}$, $OR^{313}$, $SR^{314}$ and $R^{315}$,
wherein
$R^{310}$, $R^{311}$, $R^{312}$, $R^{313}$, $R^{314}$ and $R^{315}$ are $C_{1-20}$-alkyl, $C_{2-20}$-alkenyl, $C_{2-20}$-alkynyl, $C_{5-8}$-cycloalkyl, $C_{6-14}$-aryl or heteroaryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3010}R^{3011}$, $O-R^{3012}$ and $S-R^{3013}$, and
$C_{6-14}$-aryl and heteroaryl may be substituted with one or more substituents selected from the group consisting of $C_{1-10}$-alkyl, $NR^{3014}R^{3915}$, $O-R^{3016}$ and $S-R^{3017}$,
wherein $R^{3010}$, $R^{3911}$, $R^{3012}$, $R^{3013}$, $R^{3014}$, $R^{3015}$, $R^{3016}$ and $R^{3017}$ are the same or different and are $C_{1-10}$-alkyl or phenyl,
or
$R^{13}$ and $R^{14}$ together are selected from the group consisting of

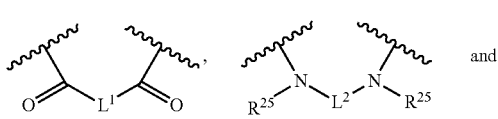

and

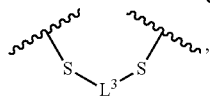

wherein

L$^1$ and L$^2$ are C$_{1-6}$-alkylene, C$_{6-14}$-arylene, or C$_{1-6}$-alkylene-C$_{6-14}$-arylene-C$_{1-6}$-alkylene, R$^{25}$ is H, C$_{1-20}$-alkyl, C$_{2-20}$-alkenyl, C$_{2-20}$-alkynyl or C$_{5-8}$-cycloalkyl, C$_{6-14}$-aryl or heteroaryl,
wherein
C$_{1-20}$-alkyl, C$_{2-20}$-alkenyl, C$_{2-20}$-alkynyl and C$_{5-8}$-cycloalkyl may be substituted with one or more substituents selected from the group consisting of phenyl, NR$^{3030}$R$^{3031}$, O—R$^{3032}$ and S—R$^{3033}$, and
C$_{6-14}$-aryl and heteroaryl may be substituted with one or more substituents selected from the group consisting of C$_{1-10}$-alkyl, NR$^{3034}$R$^{3035}$, O—R$^{3036}$ and S—R$^{3037}$,
wherein R$^{3030}$, R$^{3031}$, R$^{3032}$, R$^{3033}$, R$^{3034}$, R$^{3035}$, R$^{3036}$ and R$^{3037}$ are the same or different and are C$_{1-10}$-alkyl or phenyl, L$^3$ is a direct bond, C$_{1-6}$-alkylene, C$_{6-14}$-arylene, or C$_{1-6}$-alkylene-C$_{6-14}$-arylene-C$_{1-6}$-alkylene,
and R$^{15}$, R$^{16}$, R$^{17}$, R$^{18}$, R$^{19}$, R$^{20}$, R$^{21}$ and R$^{22}$ are the same or different and are selected from the group consisting of H, F, Cl, Br, I, CN, R$^{300}$, OR$^{301}$, SR$^{302}$, OC(O)R$^{303}$, C(O)OR$^{304}$ and NR$^{305}$R$^{306}$,
wherein R$^{300}$, R$^{301}$, R$^{302}$, R$^{303}$, R$^{304}$, R$^{305}$ and R$^{306}$ are C$_{1-20}$-alkyl, C$_{2-20}$-alkenyl, C$_{2-20}$-alkynyl, C$_{5-8}$-cycloalkyl, C$_{6-14}$-aryl or heteroaryl,
wherein
C$_{1-20}$-alkyl, C$_{2-20}$-alkenyl, C$_{2-20}$-alkynyl and C$_{5-8}$-cycloalkyl may be substituted with one or more substituents selected from the group consisting of phenyl, NR$^{3000}$R$^{3001}$, O—R$^{3002}$, S—R$^{3003}$, NO$_2$, CN and halogen, and
C$_{6-14}$-aryl and heteroaryl may be substituted with one or more substituents selected from the group consisting of C$_{1-10}$-alkyl, NR$^{3004}$R$^{3005}$, O—R$^{3006}$, S—R$^{3007}$, NO$_2$, CN and halogen,
wherein R$^{3000}$, R$^{3001}$, R$^{3002}$, R$^{3003}$, R$^{3004}$, R$^{3005}$, R$^{3006}$ and R$^{3007}$ are the same or different and are C$_{1-10}$-alkyl or phenyl,
or
R$^{17}$ and R$^{19}$, respectively, R$^{18}$ and R$^{20}$ together are

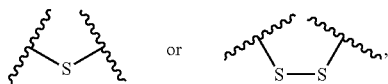

and
R$^{23}$ and R$^{24}$ together are

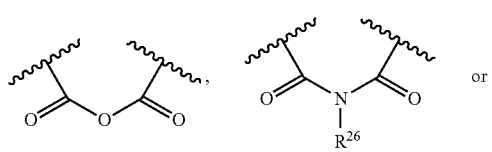

or

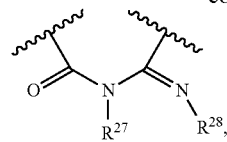

wherein

R$^{26}$, R$^{27}$ and R$^{28}$ are H, C$_{1-20}$-alkyl, C$_{2-20}$-alkenyl, C$_{2-20}$-alkynyl, C$_{5-8}$-cycloalkyl, C$_{6-14}$-aryl or heteroaryl,
wherein
C$_{1-20}$-alkyl, C$_{2-20}$-alkenyl, C$_{2-20}$-alkynyl and C$_{5-8}$-cycloalkyl may be substituted with one or more substituents selected from the group consisting of phenyl, COOM$^1$, SO$_3$M$^1$, PO$_3$M$^1$, NO$_2$, CN and halogen, and
C$_{6-14}$-aryl or heteroaryl may be substituted with one or more substituents selected from the group consisting of C$_{1-10}$-alkyl, COOM$^1$, SO$_3$M$^1$, PO$_3$M$^1$, NO$_2$, CN and halogen,
wherein M$^1$ is H, alkali metal or N(R$^{3020}$R$^{3021}$R$^{3022}$R$^{3023}$),
wherein R$^{3020}$, R$^{3021}$, R$^{3022}$, and R$^{3023}$ are the same or different and are C$_{1-10}$-alkyl,
or
R$^{27}$ and R$^{28}$ together with the unit

form a five or six membered ring which may be substituted with one or more substituents selected from the group consisting of COOM$^2$, SO$_3$M$^2$, PO$_3$M$^2$, NO$_2$, CN and halogen,
wherein M$^2$ is H, alkali metal or N(R$^{3024}$R$^{3025}$R$^{3026}$R$^{3027}$),
wherein R$^{3024}$, R$^{3025}$, R$^{3026}$, and R$^{3027}$ are the same or different and are C$_{1-10}$-alkyl, with the proviso
that if n is 0, R$^{13}$ and R$^{14}$ are phenyl, and R$^{15}$, R$^{16}$, R$^{17}$ and R$^{18}$ are H, then R$^{23}$ and R$^{24}$ together are not

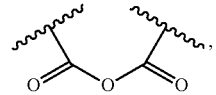 [SMILES: *C(=O)OC(*)=O]

that if n is 1, R$^{13}$ and R$^{14}$ are phenyl substituted with N(phenyl)$_2$, R$^{15}$, R$^{16}$, R$^{17}$, R$^{18}$, R$^{21}$ and R$^{22}$ are H, one of R$^{19}$ and R$^{20}$ is phenyl substituted with N(phenyl)$_2$, and the other of R$^{19}$ and R$^{20}$ is H or phenyl substituted with N(phenyl)$_2$, R$^{23}$ and R$^{24}$ together are not

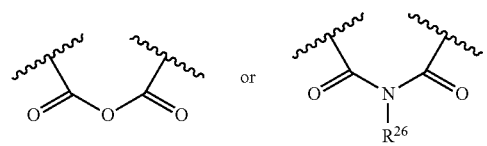

wherein R$^{26}$ is 2-ethylhexyl,
and that if n is 1, $R^{13}$ and $R^{14}$ are methyl, and $R^{15}$, $R^{16}$, $R^{17}$, $R^{18}$, $R^{19}$, $R^{20}$, $R^{21}$ and $R^{22}$ are H, then $R^{23}$ and $R^{24}$ together are not

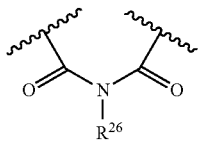

wherein $R^{26}$ is n-hexyl.

The preferences of n, $R^{13}$, $R^{14}$, $R^{15}$, $R^{16}$, $R^{17}$, $R^{18}$, $R^{19}$, $R^{20}$, $R^{21}$, $R^{22}$, $R^{23}$ and $R^{24}$ given above for the process for the preparation of compounds of formula (3), also apply to the compounds of formula (3) with the exception that for compounds of formula (3), wherein n=0, $R^{23}$ and $R^{24}$ together are preferably

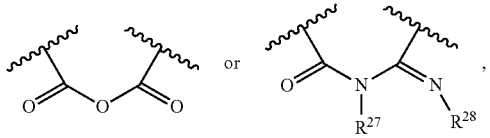

wherein
$R^{27}$ and $R^{28}$ are $C_{1-20}$-alkyl or $C_{6-14}$-aryl,
  wherein
    $C_{1-20}$-alkyl may be substituted with one or more substituents selected from the group consisting of phenyl, $COOM^1$, $SO_3M^1$, $PO_3M^1$, $NO_2$, CN and halogen, and
    $C_{6-14}$-aryl may be substituted with one or more substituents selected from the group consisting of $C_{1-10}$-alkyl, $COOM^1$, $SO_3M^1$, $PO_3M^1$, $NO_2$, CN and halogen,
      wherein $M^1$ is H, alkali metal or $N(R^{3020}R^{3021}R^{3022}R^{3023})$
        wherein $R^{3020}$, $R^{3021}$, $R^{3022}$, and $R^{3023}$ are the same or different and are $C_{1-10}$-alkyl,
or
$R^{27}$ and $R^{28}$ together with the unit

form a five or six membered ring which may be substituted with one or more substituents selected from the group consisting of $COOM^2$, $SO_3M^2$, $PO_3M^2$, $NO_2$, CN and halogen,
  wherein $M^2$ is H, alkali metal or $N(R^{3024}R^{3025}R^{3026}R^{3027})$
    wherein $R^{3024}$, $R^{3025}$, $R^{3026}$, and $R^{3027}$ are the same or different and are $C_{1-10}$-alkyl,
more preferably

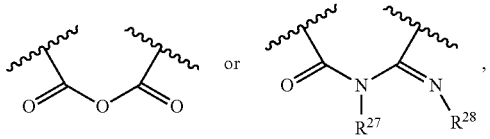

wherein
$R^{27}$ and $R^{28}$ are $C_{1-20}$-alkyl or $C_{6-14}$-aryl,
  wherein
    $C_{1-20}$-alkyl may be substituted with one or more substituents selected from the group consisting of phenyl and $COOM^1$, and
    $C_{6-14}$-aryl may be substituted with one or more substituents selected from the group consisting of $C_{1-10}$-alkyl, $COOM^1$,
      wherein $M^1$ is H, alkali metal or $N(R^{3020}R^{3021}R^{3022}R^{3023})$,
        wherein $R^{3020}$, $R^{3021}$, $R^{3022}$, and $R^{3023}$ are the same or different and are $C_{1-10}$-alkyl,
or
$R^{27}$ and $R^{28}$ together with the unit

form a five or six membered ring which may be substituted with one or more substituents selected from the group consisting of $COOM^2$ and CN,
  wherein $M^2$ is H, alkali metal or $N(R^{3024}R^{3025}R^{3026}R^{3027})$
    wherein $R^{3024}$, $R^{3025}$, $R^{3026}$, and $R^{3027}$ are the same or different and are $C_{1-10}$-alkyl;
most preferably

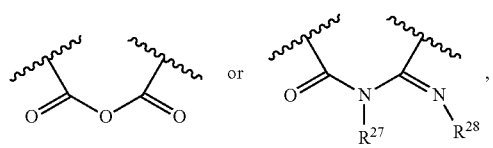

wherein
$R^{27}$ and $R^{28}$ are $C_{1-20}$-alkyl or $C_{6-14}$-aryl,
  wherein
    $C_{1-20}$-alkyl may be substituted with $COOM^1$,
      wherein $M^1$ is H,
or
$R^{27}$ and $R^{28}$ together with the unit

form a five membered ring which may be substituted with one or more substituents selected from the group consisting of $COOM^2$ and CN,
  wherein $M^2$ is H.

Preferred are the compounds of formulae
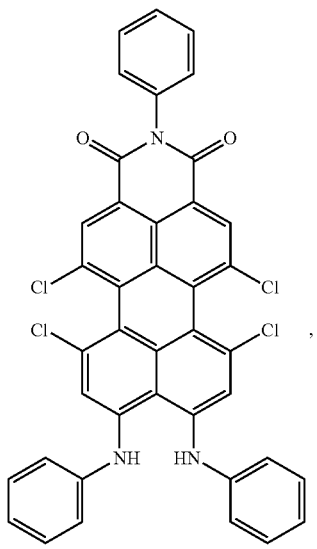
(3a)
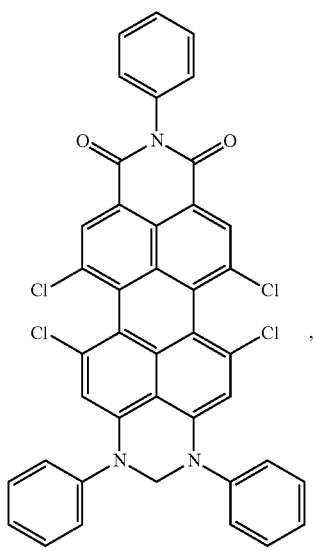
(3b)
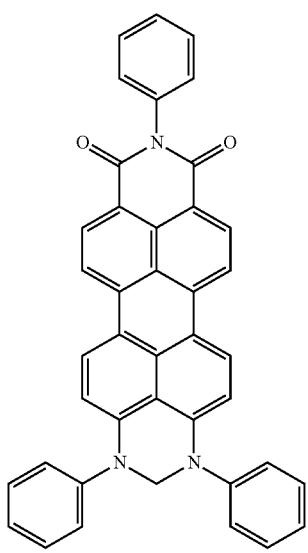
(3c)
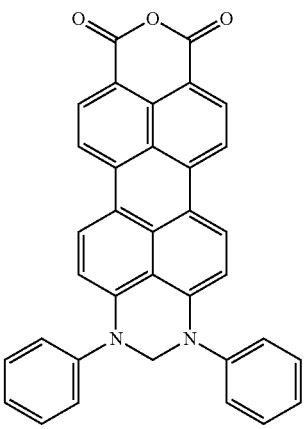
(3d)
,
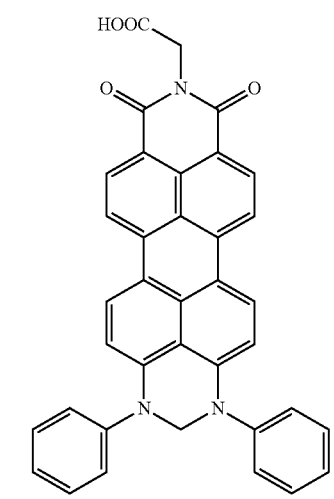
(3e)
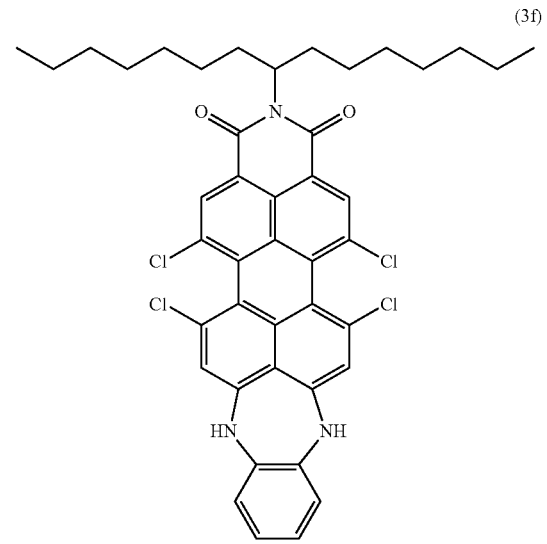
(3f)

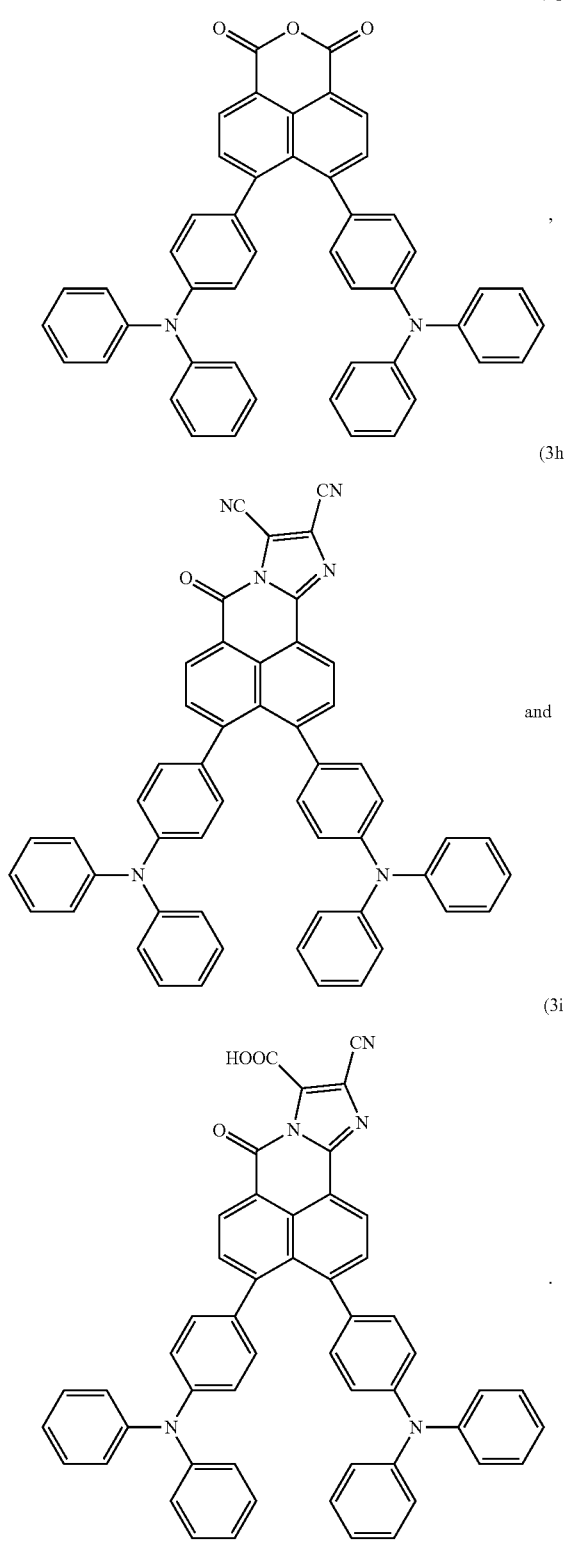

The compounds of formula (3) can be used in various applications, for example as colorants or in electronic devices such in organic field-effect transistors, organic light emitting devices and in photovoltaic devices such as dye-sensitized solar cells (DSCs).

The compounds of formulae 3a, 3b, 3c, 3d, 3e and 3i show a broad absorption in the wavelength range from about 400 to 750 nm. The compounds of formulae 3e and 3i carrying a COOH anchor group and the compounds of formulae 3d and 3g carrying an anhydride anchor group are particular suitable as dyes for dye-sensitized solar cells (DSCs).

Also part of the invention is the use of the compounds of formula (3) in electronic devices.

The process of the present invention is advantageous as it allows the convenient preparation of compounds of formula (3).

The key intermediates of the process of the present invention for the preparation of the compounds of formula (3) are the compounds of formula (1) carrying two X-groups, wherein X is Cl, Br or I, in the 9 and 10-positions (if n is 1), or in the 4 and 5 positions (if n is 0). The compounds of formula (1) are versatile building blocks, which allow the easy and introduction of various substituents in the 9 and 10-positions (if n is 1), or in the 4 and 5 positions (if n is 0) by methods known in the art. In case, the compounds of formula (1) also carry suitable substituents such as Cl in the $R^1$, $R^2$, $R^3$, $R^4$, $R^5$, $R^6$, $R^7$ and/or $R^8$ positions, these substituents can also be easily replaced with other substituents.

The compounds of formula (1) can be prepared in a very convenient and economic manner from the compounds of formula (2). The compounds of formula (2), especially the compounds of formula (2), wherein $R^9$ and $R^{10}$, respectively $R^{11}$ and $R^{12}$ together are

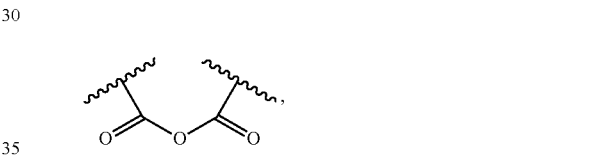

are readily available and of low cost. The compounds of formula (1) are usually obtained in high yields (for example higher than 80%). The X-groups are selectively introduced in 9 and 10 positions (if n is 1) and the 4 and 5 positions (if n is 0). Steps a), b) and c) can be performed at moderate temperatures, for example at temperatures below 120° C. In addition, steps a), b) and c) can be performed in an aqueous solvent such as water, and in a so-called "one pot reaction".

EXAMPLES

Example 1

Preparation of Compound 1a

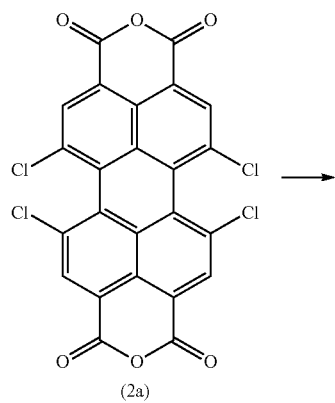

(2a)

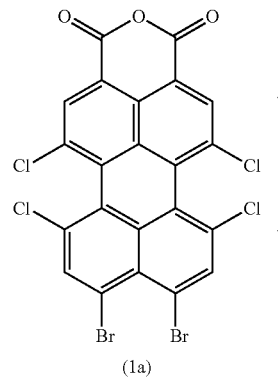

(1a)

Figure 1:
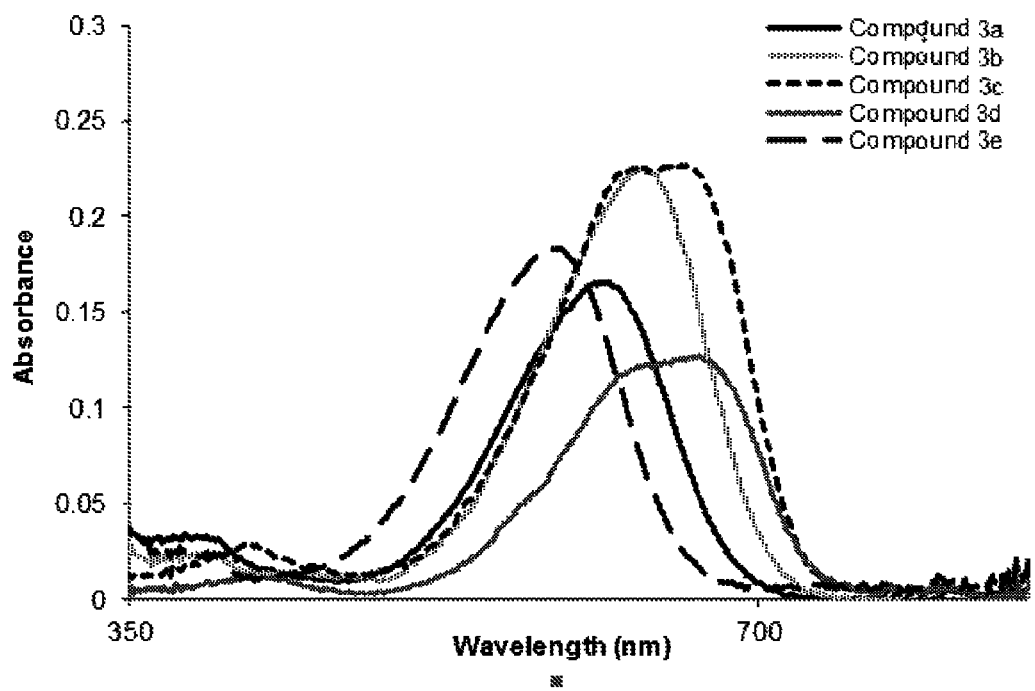
FIG. 1 shows the absorbance of the compounds of formulae 3a, 3b, 3c, 3d and 3e in dichloromethane against the wavelength in the range of 350 to 800 nm.

30 ml 1M NaOH was added to a suspension of compound 2a (2.65 g, 5.00 mmol) in 100 ml water and the mixture was stirred to obtain a limpid solution. The mixture was heated (80° C.) and 30 mmol acetic acid was added. Bromine (11 mmol, 0.57 ml) was added in one portion and the reaction mixture was stirred at 80° C. for 2 h. The precipitate was filtered, washed with water and dried. The solid was suspended in 50 ml methanol and 50 ml acetic acid and stirred for 5 h at 100° C. The mixture was poured in methanol (200 ml) and precipitate was filtered, washed with methanol and dried. Yield 2.65 g (86%). FD mass spectrum (8 kV): m/z (%): calcd for 617.89. found: 616.8. $^1$H NMR (300 MHz, $C_2D_2Cl_4$, 300K): 8.20 (s, 2H); 8.63 (s, 2H). Elemental analysis calcd (%) for $C_{22}H_4Br_2C_{14}N_3O_3$: C, 42.76; H, 0.65. found: C, 42.76; H, 0.66.

Example 2

Preparation of Compound 3a

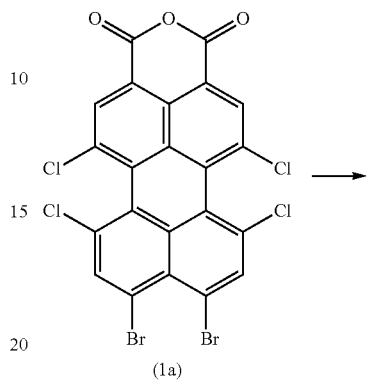

(1a)

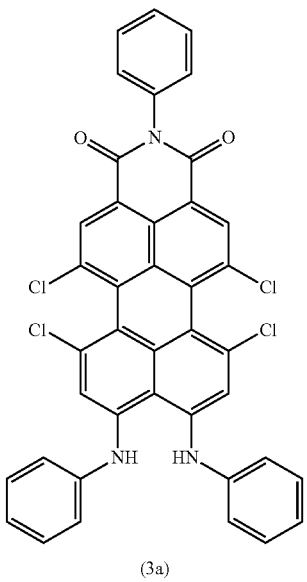

(3a)

A suspension of compound 1a (0.64 g, 2.0 mmol) in 8 ml aniline was stirred at 180° C. under argon for 5 h. The mixture was poured into 10% hydrochloric acid and ice. The precipitate was filtered, washed with water and water/methanol 1:1. Crude compound 3a was purified by column chromatography using dichloromethane as eluent on silica. Yield 1.01 g (70%). $^1$H NMR (300 MHz, $C_2D_2Cl_4$, 300K): 7.17-7.22 (m, 6H); 7.33-7.35 (m, 2H); 7.34 (s, 2H); 7.40-7.46 (m, 4H); 7.52-7.63 (m, 3H); 7.86 (s, 2H, NH) 8.56 (s, 2H). $^{13}$C NMR (75.0 MHz, $C_2D_2Cl_4$, 300K): 113.86 (1C); 116.13 (2C); 116.85 (2C); 119.37 (2C); 121.15 (4C); 123.61 (1C); 124.53 (2C); 128.76 (1C); 129.37 (2C); 129.90 (4C); 130.64 (2C); 131.64 (2C); 131.83 (1C); 132.55 (2C); 135.04 (1C); 135.86 (1C); 137.75 (2C); 140.53 (2C); 145.27 (2C); 163.07 (2C, CO). FD mass spectrum (8 kV): m/z (%): calcd for 717.43. found: 715.7 (100) [M]$^+$. Elemental analysis calcd (%) for $C_{40}H_{21}CL_4N_3O_2$: C, 66.97; H, 2.95; N, 5.86. found: C, 66.41; H, 3.08; N, 5.86. UV-Vis ($CH_2Cl_2$): $\lambda_{max}$=615 (33 163) nm ($M^{-1}$ $cm^{-1}$).

Example 3

Preparation of Compound 3b

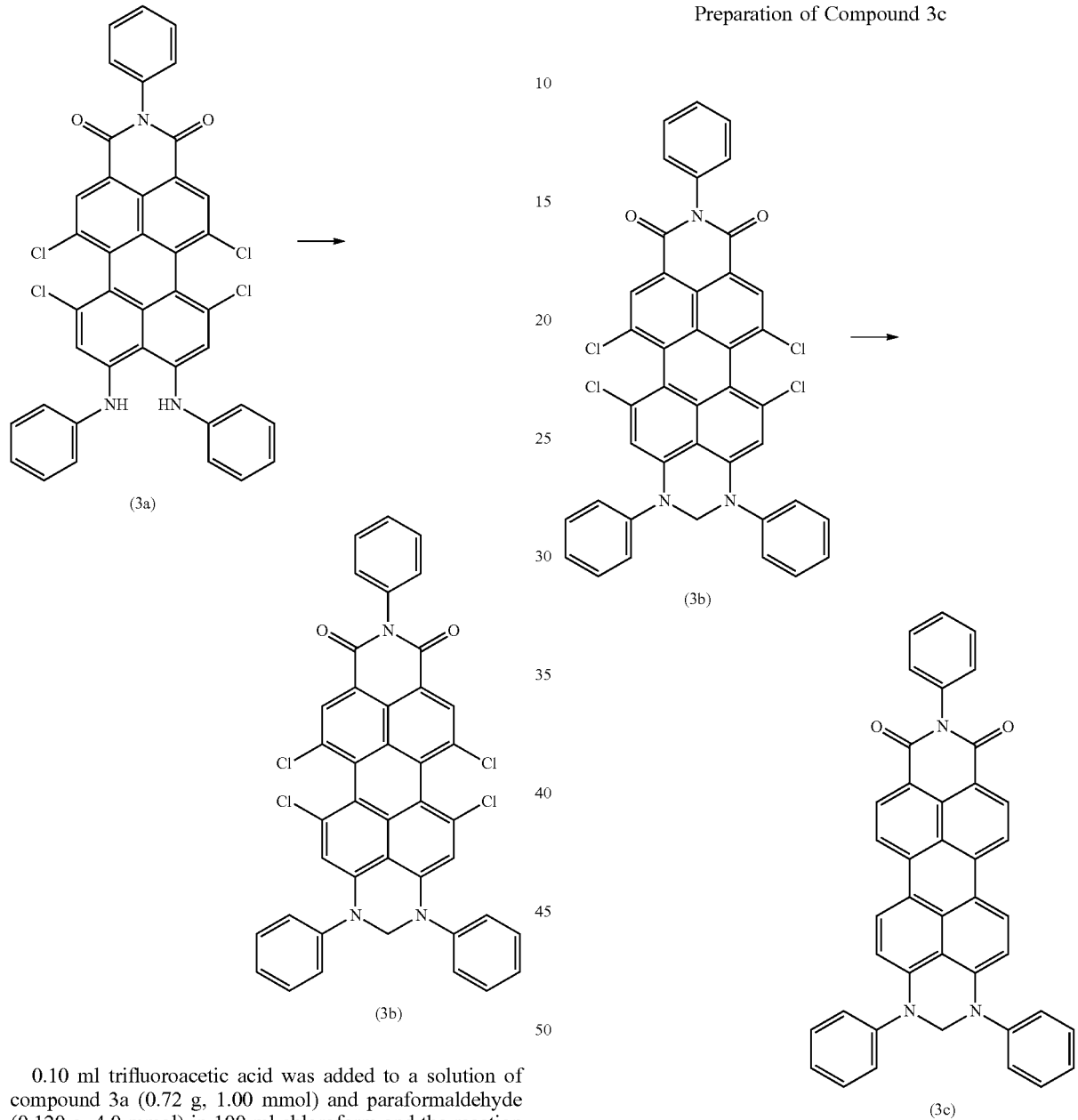

(3a)

(3b)

0.10 ml trifluoroacetic acid was added to a solution of compound 3a (0.72 g, 1.00 mmol) and paraformaldehyde (0.120 g, 4.0 mmol) in 100 ml chloroform and the reaction mixture was refluxed for 1.5 h under argon. The solvent was removed under vacuum and the crude solid was purified by column chromatography using dichloromethane as eluent on silica. Yield 0.70 g (96%). $^1$H NMR (300 MHz, C$_2$D$_2$Cl$_4$, 300K): 5.38 (s, 2H, CH$_2$); 6.91 (s, 2H); 7.33-7.45 (m, 8H); 7.53-7.62 (m, 7H); 8.56 (s, 2H). $^{13}$C NMR (75.0 MHz, C$_2$D$_2$Cl$_4$, 300K): 67.21 (1C, CH$_2$); 109.65 ((1C)); 109.87 ((2C)); 114.44 ((2C)); 118.65 ((2C)); 124.09 ((1C)); 124.75 ((4C)); 127.33 ((2C)); 128.68 ((2C)); 129.34 ((2C)); 129.52 ((2C)); 130.32 ((4C)); 131.77 ((2C)); 131.87 ((1C)); 132.55 ((1C)); 133.98 ((1C)); 135.20 ((1C)); 138.45 ((2C)); 142.02 ((2C)); 144.59 ((2C)); 163.15 ((2C, CO). FD mass spectrum (8 kV): m/z (%): calcd for 729.44. found: 729.5 (100) [M]$^+$.

Elemental analysis calcd (%) for C$_{41}$H$_{21}$O$_4$N$_3$O$_2$: C, 67.51; H, 2.90; N, 5.76. found: C, 67.44; H, 2.83; N, 5.79. UV-Vis (CH$_2$Cl$_2$): $\lambda_{max}$=635 (45 092) nm (M$^{-1}$ cm$^{-1}$).

Example 4

Preparation of Compound 3c (3b)

(3c)

A mixture of potassium hydroxide (3.0 g) and compound 3b (0.68 g, 1.08 mmol) in 30 ml 1,2-ethanediol was stirred an heated at 165° C. for 4 h. The mixture was cooled and diluted with 50 ml 10% hydrochloric acid. The precipitate was filtered, washed with water and dried. The crude solid was purified by column chromatography using dichloromethane/acetone as eluent on silica. Yield 0.40 g (63%). $^1$H NMR (300 MHz, C$_2$D$_2$Cl$_4$, 300K): 5.37 (s, 2H, CH$_2$); 6.87 (d, 2H, $^3$J$_{HH}$=8.6 Hz); 7.25-7.39 (m, 8H); 7.45-7.55 (m, 7H); 7.83 (d, 2H, $^3$J$_{HH}$=8.5 Hz); 8.11 (d, 2H, $^3$J$_{HH}$=8.9 Hz); 8.29 (d, 2H, $^3$J$_{HH}$=8.2 Hz). $^{13}$C NMR (75.0 MHz, C$_2$D$_2$Cl$_4$, 300K): 67.06 (1C, CH$_2$); 108.56 (2C); 114.10 (1C); 116.55

(1C); 116.77 (2C); 119.34 (2C); 124.60 (4C); 125.75 (1C); 126.31 (2C); 126.92 (2C); 128.13 (1C); 128.70 (2C); 128.84 (2C); 129.06 (2C); 129.94 (4C); 130.90 (1C); 131.32 (2C); 136.00 (1C); 138.66 (2C); 143.04 (2C); 144.83 (2C); 163.99 (2C, CO). FD mass spectrum (8 kV): m/z (%): calcd for 591.66. found: 591.9 (100) [M]$^+$. UV-Vis (CH$_2$Cl$_2$): $\lambda_{max}$=655 (45 398) nm (M$^{-1}$ cm$^{-1}$).

Example 5

Preparation of Compound 3d

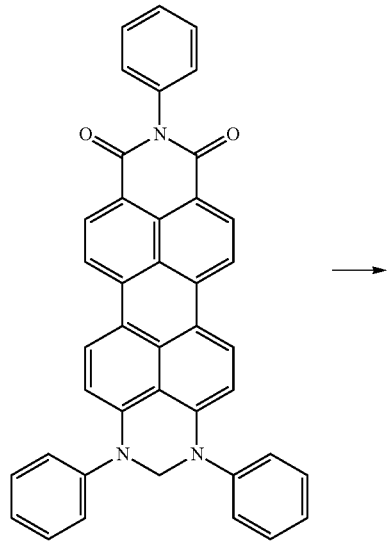

(3c)

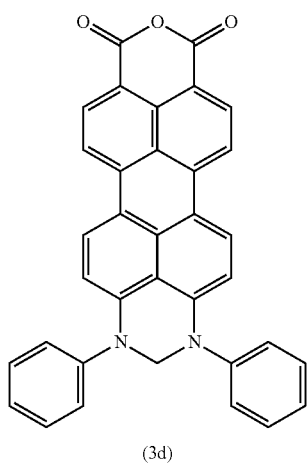

(3d)

Potassium hydroxide (1.0 g) was added to a solution of compound 3c (0.30 g, 0.51 mmol) in tert-buthanol (30 ml) and 1,4-dioxane (10 ml), and the reaction mixture was refluxed overnight under argon. The mixture was poured into 10% hydrochloric acid and ice. The precipitate was filtered, washed with water and water/methanol 1:1. The crude product was dissolved in THF/AcOH (5:1) and reflux for 5 h. The solvent was removed under reduced pressure and crude compound 3d was used without further purification Yield 0.25 g (95%). FD mass spectrum (8 kV): m/z (%): calcd for 516.54. found: 516.3 (100) [M]$^+$.

Example 6

Preparation of Compound 3e

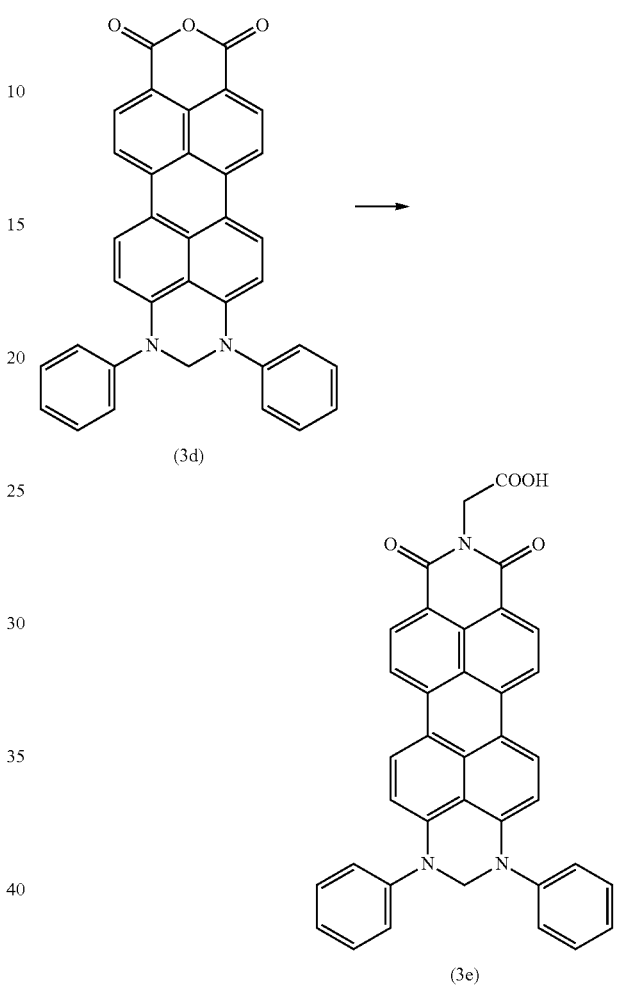

A mixture of compound 3d (0.25 g, 0.48 mmol), glycine (0.20 g) and imidazole (2.0 g) was stirred at 140° C. under argon atmosphere for 4 h. The mixture was poured into 10% hydrochloric acid and ice. The precipitate was filtered, washed with water and water/methanol 1:1. Crude compound 3e was dissolved in THF and precipitated in water/methanol 1:2. Yield 0.24 g (87%). $^1$H NMR (300 MHz, DMSO-d$_6$, 300K): 4.65 (s, 2H, CH$_2$COOH); 5.38 (s, 2H, NCH$_2$N); 6.78 (d, 2H, $^3J_{HH}$=8.6 Hz); 7.27-7.35 (m, 2H); 7.45-7.56 (m, 8H); 7.92 (d, 2H, $^3J_{HH}$=8.5 Hz); 8.04 (d, 2H, $^3J_{HH}$=8.3 Hz); 8.25 (d, 2H, $^3J_{HH}$=8.9 Hz); 12.93 (bs, 1H, COOH). $^{13}$C NMR (75.0 MHz, DMSO-d$_6$, 300K): 40.88 (1C, CH$_2$COOH); 66.81 (1C, NCH$_2$N); 108.62 (2C); 113.78 (1C); 115.73 (2C); 116.85 (1C); 118.82 (2C); 124.24 (4C); 125.09 (1C); 125.95 (2C); 127.72 (2C); 128.27 (1C); 129.86 (4C); 129.94 (2C); 130.86 (2C); 138.19 (2C); 143.01 (2C); 144.58 (2C); 162.50 (2C, CO); 169.66 (1C, COOH). FD mass spectrum (8 kV): m/z (%): calcd for 573.60. found: 573.6 (100) [M]$^+$. UV-Vis (CH$_2$Cl$_2$): $\lambda_{max}$=667 (25 505) nm (M$^{-1}$ cm$^{-1}$).

Example 7

Preparation of Compound 1b

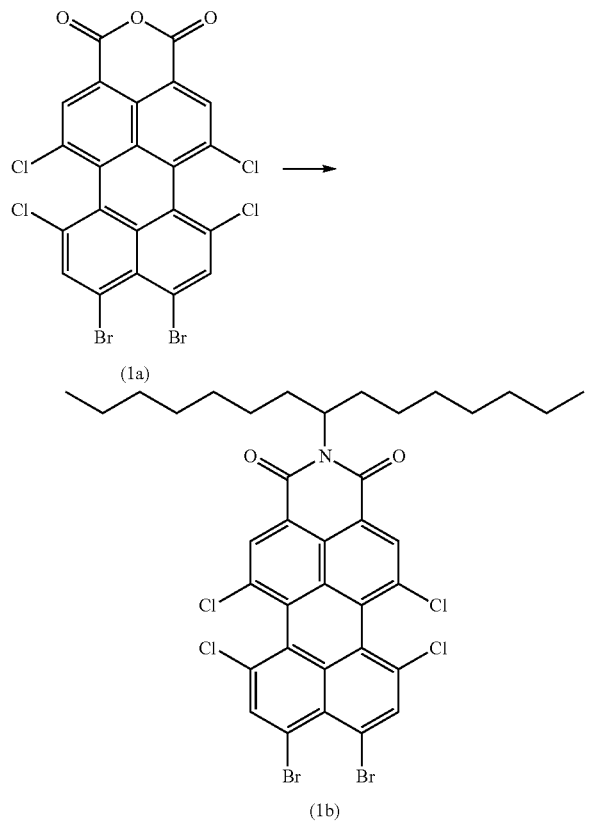

Pentadecan-8-amine (4.0 mmol, 0.91 g) was added to a suspension of compound 1a (2.0 mmol, 1.24 g) in 20 ml NMP and 10 ml acetic acid. The reaction mixture was stirred at 110° C. for 15 h. After cooling down to room temperature the reaction mixture was poured in water. The precipitate was filtered, washed with methanol, dried and purified by column chromatography using hexane/dichloromethane as eluent on silica. (0.80 g, 48%). FD-Mass: calc.: 827.30. found: 829.3. $^1$H-NMR (δ (ppm), CDCl$_3$): 0.84 (t, 6H, CH$_3$, $^3J_{HH}$=7.3 Hz); 1.78-1.92 (m, 2H, CH$_2$); 2.07-2.22 (m, 2H, CH$_2$); 4.89-4.99 (m, 1H, CHN); 8.08 (s, 2H, H-8 and 11); 8.49 (s, 2H, H-2 and 5).

Example 8

Preparation of Compound 3f

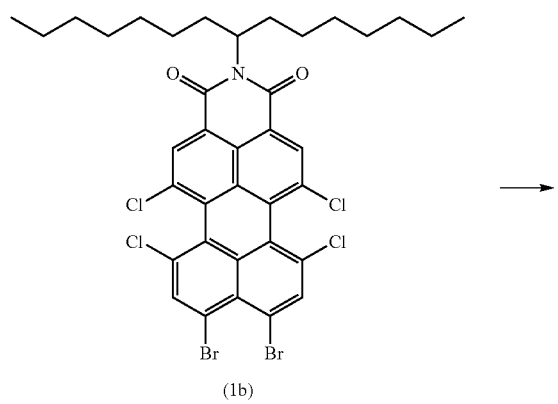

A mixture of compound 1 b (0.415 g, 0.5 mmol), and 1,2-diaminobenzene (0.22 g, 2.0 mmol) in 10 ml NMP was stirred at 180° C. under argon for 5 h. The mixture was poured into 10% hydrochloric acid and ice. The precipitate was filtered, washed with water and methanol. Crude compound 3f was purified by column chromatography using dichloromethane as eluent on silica. Yield 0.17 g (43%). $^1$H NMR (300 MHz, C$_2$D$_2$Cl$_4$, 300K): 0.84 (t, 6H, CH$_3$, $^3J_{HH}$=5.9 Hz); 1.14-1.36 (m, 20H, CH$_2$); 1.80-1.91 (m, 2H, CH$_2$); 2.15-2.27 (m, 2H, CH$_2$); 5.09-5.21 (m, 1H, CHN); 6.34 (s, 2H, NH); 6.88 (s, 1H); 6.90 (s, 1H); 6.97-7.07 (m, 4H); 8.50 (s, 1H) 8.53 (s, 1H). $^{13}$C NMR (75.0 MHz, C$_2$D$_2$Cl$_4$, 300K): 14.07 (2C CH$_3$); 22.53 (2C, CH$_2$); 26.86 (2C, CH$_2$); 29.09 (2C, CH$_2$); 29.43 (2C, CH$_2$); 31.71 (2C, CH$_2$); 32.21 (2C, CH$_2$); 54.63 (1C, CHN); 109.07; 116.12; 116.20; 119.83; 123.27; 123.99; 130.50; 130.69; 130.92; 132.18; 132.84; 135.86; 136.75; 143.73; 162.92 (1C, CO); 164.05 (1C, CO). FD-Mass: calc.: 773.62. found: 772.7. UV-Vis (CH$_2$Cl$_2$): λ$_{max}$=588 (36 654) nm (M$^{-1}$ cm$^{-1}$).

Example 9

Preparation of Compound 1C

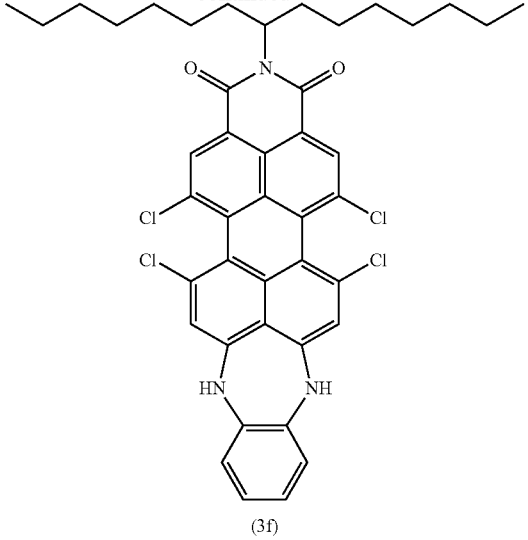

20 ml (20 mmol) 1M NaOH was added to a suspension of compound 2b (4.00 mmol) in 20 ml water and the mixture was stirred to obtain a limpid solution. The mixture was heated (90-95° C.) and 20 mmol acetic acid was added. Bromine (0.5 ml, 1.56 g, 10 mmol, 2.5 equiv) was added in one portion and the reaction mixture was stirred at 90-95° C. for 24 h. The precipitate was filtered, washed with acetone and dried. Yield 1.35 g (95%). Purity >85%.

Example 10

Preparation of Compound 3g

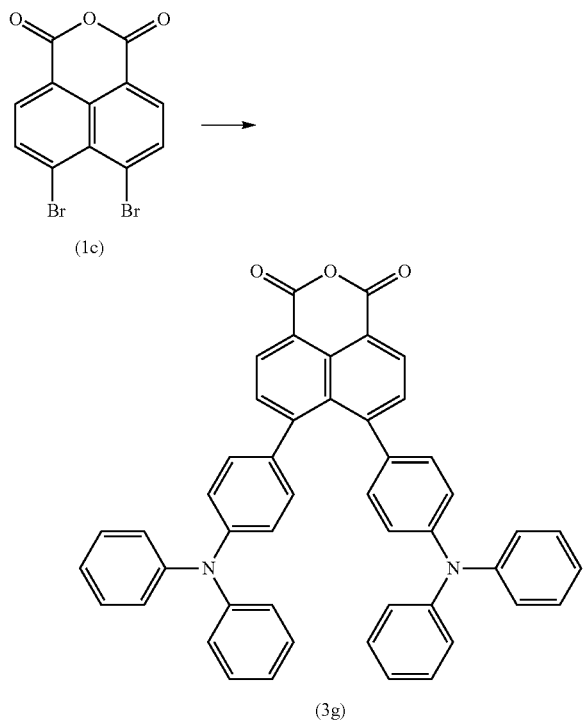

Pd[P(Ph)$_3$]$_4$ (3 mol %) was added to a mixture of compound 1c (2.00 mmol), 4-(diphenylamino)phenylboronic acid (3.5 mmol), 10 ml 1M K$_2$CO$_3$ (10.0 mmol) in 50 ml 1,4-dioxane under argon atmosphere. The mixture was stirred at 95° C. under argon atmosphere for 6 h. The solvent was removed under reduced pressure. The solid was dissolved in acetic acid and dichloromethane and reflux overnight. The solvent was removed under reduced pressure. Crude compound 3g was purified by column chromatography using dichloromethane as eluent on silica. Yield 1.065 g (78%). FD-Mass: calc.: 684.78. found: 683.1. $^1$H-NMR (δ (ppm), CD$_2$Cl$_2$): 6.75-6.78 (m, 4H); 6.82-6.85 (m, 4H); 6.96-7.02 (m, 4H); 7.05-7.08 (m, 8H); 7.15-7.20 (m, 8H); 7.78 (d, 2H, $^3J_{HH}$=7.7 Hz); 8.56 (d, 2H, $^3J_{HH}$=7.7 Hz). $^{13}$C-NMR (δ (ppm), CD$_2$Cl$_2$): 117.63 (2C); 121.11 (4C); 124.28 (4C); 125.95 (8C); 128.71 (1C); 130.00 (8C); 131.12 (4C); 131.64 (2C); 133.12 (2C); 133.58 (1C); 134.79 (2C); 147.75 (4C); 147.91 (2C); 149.91 (2C); 161.67 (2C, CO).

Example 11

Preparation of Compound 3h

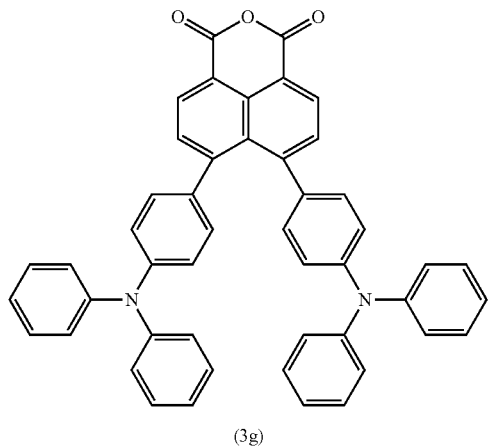

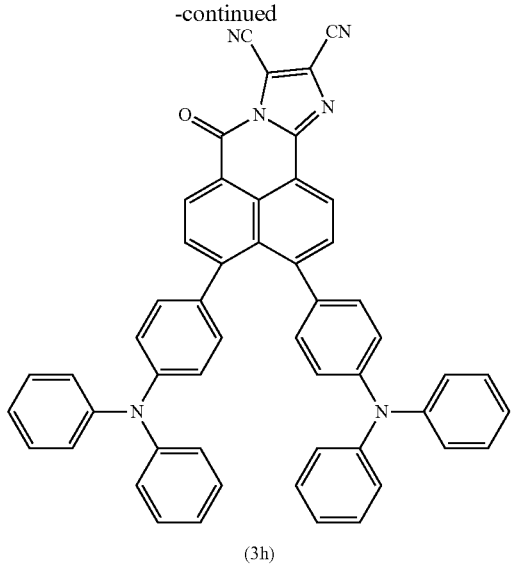

A mixture of compound 3g (0.60 g, 0.88 mmol), 2,3-diaminomaleonitrile (0.38 g, 3.5 mmol), CaO (20 eq) in 20 ml pyridine was stirred and reflux under argon atmosphere for 24 h. The solvent was removed under reduced pressure. Crude compound 3h was purified by column chromatography using hexane/dichloromethane as eluent on silica. Yield 0.130 g (24%). $^1$H-NMR (δ (ppm), CDCl$_3$): 6.78-6.89 (m, 8H); 6.98-7.03 (m, 4H); 7.08-7.10 (m, 8H); 7.15-7.21 (m, 8H); 7.74 (d, 1H, $^3J_{HH}$=7.8 Hz); 7.79 (d, 1H, $^3J_{HH}$=7.8 Hz); 8.72 (d, 1H, $^3J_{HH}$=7.8 Hz); 8.81 (d, 1H, $^3J_{HH}$=7.8 Hz). $^{13}$C-NMR (δ (ppm), CDCl$_3$): 107.72; 108.24; 111.42; 116.43; 118.71; 120.51; 120.67; 124.00; 124.14; 125.60; 125.70; 126.93; 128.70; 128.76; 129.23; 129.64; 129.66; 130.89; 131.01; 131.56; 131.60; 134.05; 134.29; 147.09; 147.20; 147.49; 147.87; 148.54; 149.15; 152.38; 157.97.

Example 12

Preparation of compound 3i

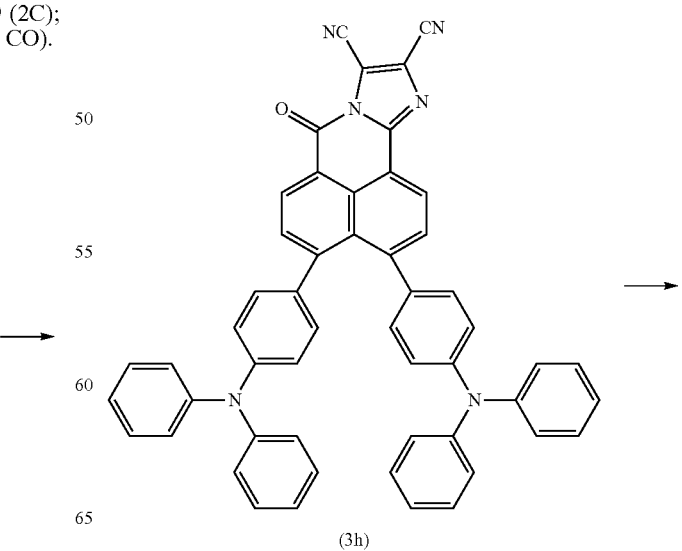

-continued

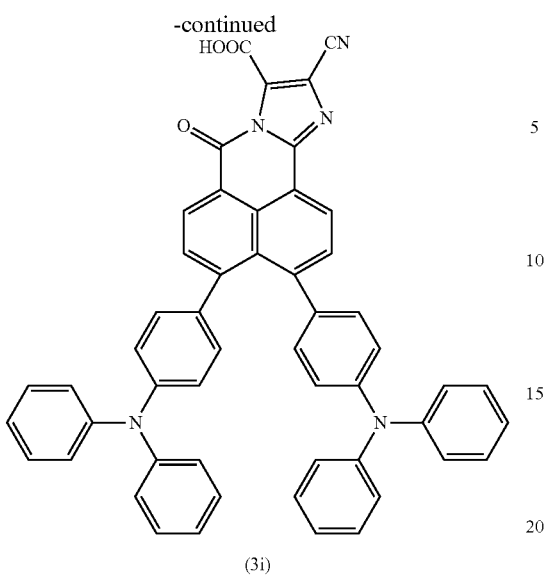

(3i)

NaOH (1.0 g) in 3 ml of water was added to a solution of compound 3h (130 mg, 0.17 mmol) in 1,4-dioxane (15 ml). The reaction mixture was stirred at 70° C. overnight. The reaction mixture was cooled down to room temperature and poured into diluted HCl. The precipitate was filtered, washed and dried. Crude compound 3i was purified by recrystallization of methanol. Yield 0.10 g (74%). $^1$H-NMR (δ (ppm), DMSO-$d_6$): 6.75-6.78 (m, 4H); 6.99-7.13 (m, 16H); 7.27-7.33 (m, 8H); 7.89 (d, 1H, $^3J_{HH}$=7.9 Hz); 7.92 (d, 1H, $^3J_{HH}$=7.9 Hz); 8.12 (s, 1H, COOH); 8.74 (d, 1H, $^3J_{HH}$=7.7 Hz); 8.80 (d, 1H, $^3J_{HH}$=7.8 Hz). $^{13}$C-NMR (δ (ppm), DMSO-$d_6$): 101.27; 110.75; 117.78; 120.06; 120.12; 120.24; 123.77; 123.89; 124.75; 124.87; 126.96; 127.78; 128.32; 129.61; 130.72; 130.85; 131.30; 132.48; 134.27; 134.58; 145.61; 146.23; 146.57; 146.65; 147.20; 147.36; 149.49; 158.69; 161.07.

Example 13

The absorbance of the compounds of formulae 3a, 3b, 3c, 3d and 3e in dichloromethane were measured in the wavelength range of 350 to 800 nm. The results are shown in FIG. 1.

Example 14

Preparation of Solid-State Dyesensitized Solar Cells (ssDSCs) Comprising the Compound of Formula (3e) as Dye A TiO$_2$ blocking layer was prepared on a fluorine-doped tin oxide (FTO)-covered glass substrate using spray pyrolysis (Peng, B.; Jungmann, G.; Jager, C.; Haarer, D.; Schmidt, H. W.; Thelakkat, M. Coord. Chem. Rev. 2004, 248, 1479). Then, a TiO$_2$ paste (Dyesol), diluted with terpineol, was applied by screen printing, resulting in a film thickness of 1.7 μm. All films were then sintered for 45 min at 450° C., followed by treatment in a 40 mM aqueous solution of TiCl$_4$ at 60° C. for 30 min, followed by another sintering step. The so obtained FTO-covered glass substrates with TiO$_2$ layers were pretreated with 5 mM solutions of the 2-(p-butoxyphenyl)acetohydroxamic acid sodium salt in ethanol (2-(p-butoxyphenyl)acetohydroxamic acid sodium salt is described on page 52 of WO 2012/001628 A1 as "Example No. 6"), followed by dyeing in a 0.5 mM solution of a compound of formula (3e) in CH$_2$Cl$_2$. Then, 2,2',7,7'-tetrakis-(N,N-di-p-methoxyphenyl amine)-9,9'-spirobifluorene (Spiro-MeOTAD) was applied by spin-coating from a solution in CH$_2$Cl$_2$ (200 mg/mL) also containing 20 mM Li(CF$_3$SO$_2$)$_2$N. Fabrication of the ssDSCs was completed by evaporation of 200 nm of silver as the counter electrode. The active area of the ssDSCs was defined by the size of these contacts (0.13 cm$^2$), and the ssDSC was masked by an aperture of the same area for measurements.

Example 15

Preparation of a Solid-State Dyesensitized Solar Cell (ssDSC) Comprising the Compound of Formula (3i) as Dye A solid-state dyesensitized solar cell (ssDSC) comprising the compound of formula (3i) as dye was prepared in analogy to example 14.

Example 16

The absorbance of the devices of examples 14 and 15, both before the fabrication of the ssDSCs was completed by evaporation of 200 nm of silver as the counter electrode, against the wavelength were measured.

Figure 2:
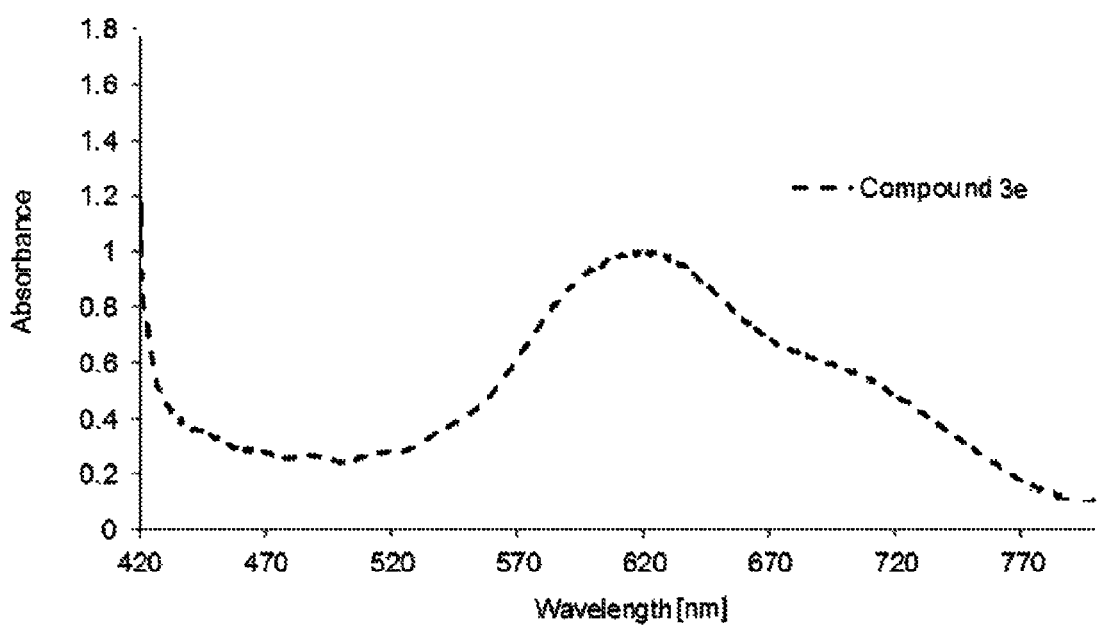
FIG. 2 shows the absorbance of the device of example 14 comprising the compound of formula 3e, before the fabrication of the solid-state dye-sensitized solar cell (ssDSC) was completed by evaporation of 200 nm of silver as the counter electrode, against the wavelength.

The plot of the absorbance of the device of examples 14, comprising the compound of formula 3e, before the fabrication of the ssDSCs was completed by evaporation of 200 nm of silver as the counter electrode, against the wavelength is shown in FIG. 2.

Figure 5:
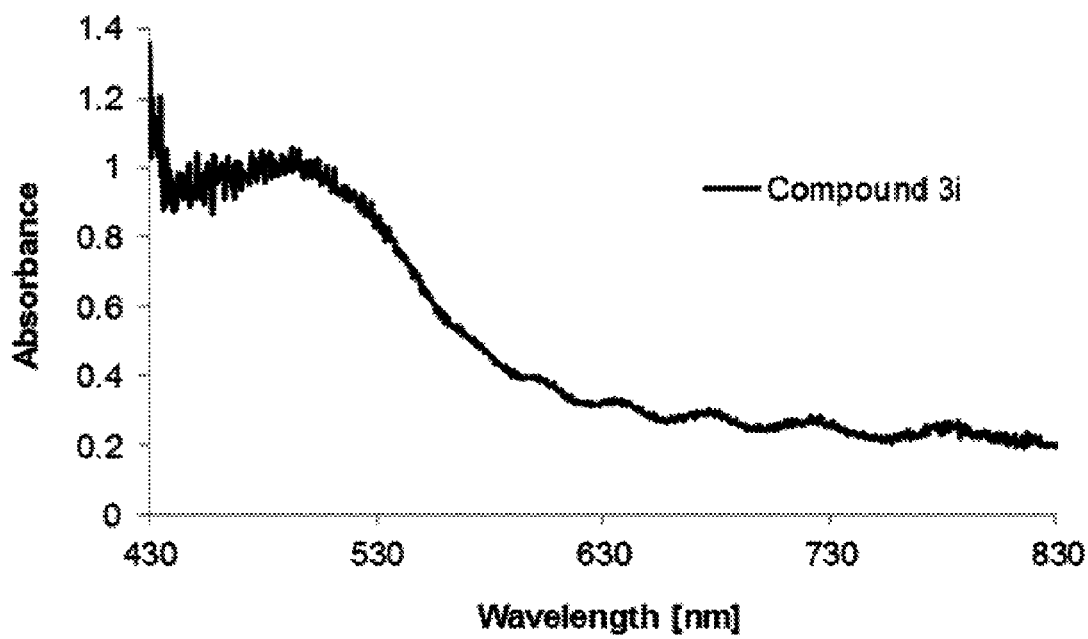
FIG. 5 shows the absorbance of the device of example 15 comprising the compound of formula 3i, before the fabrication of the solid-state dye-sensitized solar cell (ssDSC) was completed by evaporation of 200 nm of silver as the counter electrode, against the wavelength.

The plot of the absorbance of the device of examples 15 comprising the compound of formula 3i, before the fabrication of the ssDSC was completed by evaporation of 200 nm of silver as the counter electrode, against the wavelength is shown in FIG. 5.

Example 17

The current-voltage characteristics for the ssDSCs of examples 14 and 15 were measured with a Keithley 2400 under 1000 W/m$^2$, AM 1.5G conditions (LOT ORIEL 450 W).

Figure 3:
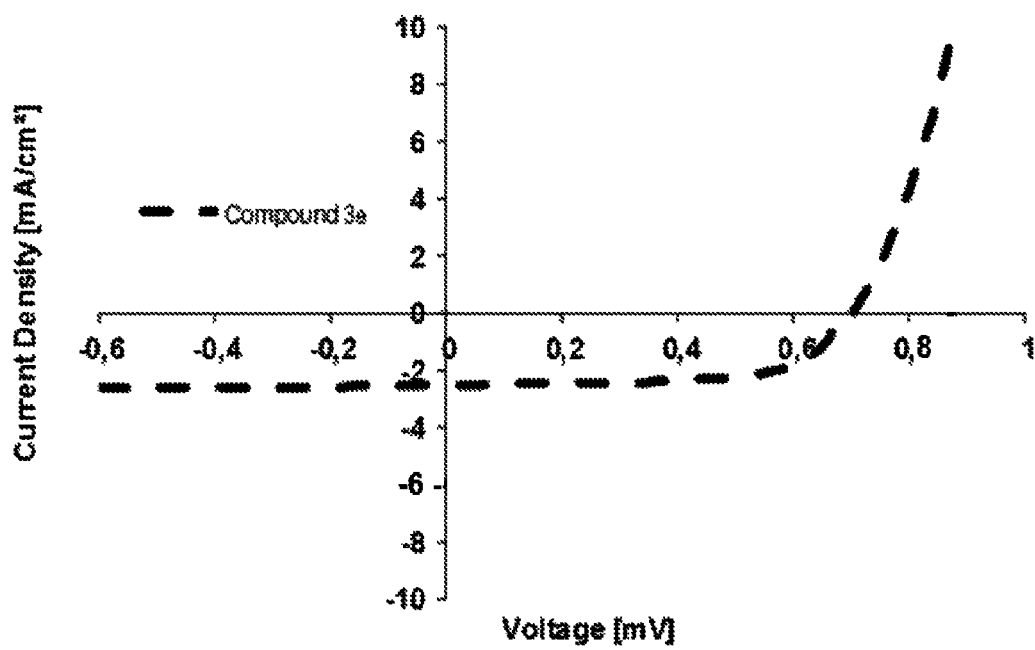
FIG. 3 shows the current density I against the voltage of the solid-state dye-sensitized solar cell (sDSC) of example 14 comprising the compound of formula 3e.

The plots of the current density I against the voltage of the ssDSC of example 14 is shown in FIG. 3.

Figure 6:
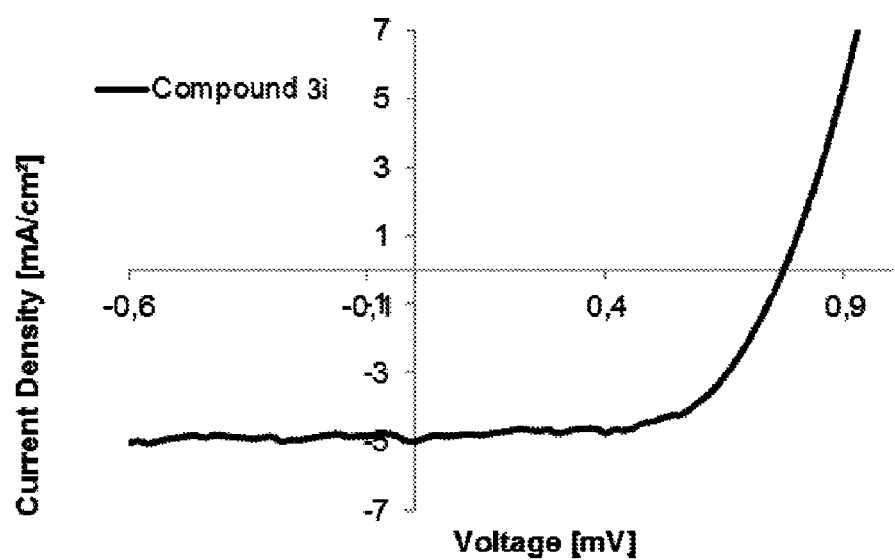
FIG. 6 shows the current density I against the voltage of the solid-state dye-sensitized solar cell (ssDSC) of example 15 comprising the compound of formula 3i.

The plot of the current density I against the voltage of the ssDSC of example 15 is shown in FIG. 6.

The short circuit current Isc, the open circuit voltage Voc, the power conversion efficiency ETA, and the fill factor FF of the ssDCSs of examples 14 and 15 were determined.

The short circuit Isc is I at V=0.

The open circuit Voc is V at I=0.

The fill factor FF is $(I_{mpp} \times V_{mpp})/(I_{SC} \times V_{OC})$, wherein mpp is the maximum power point.

The power conversion efficiency ETA is the percentage of the solar energy to which the cell is exposed that is converted into electrical energy.

The results are shown in table 1.

TABLE 1

| ssDCS | compound | $I_{SC}$ [mA/cm$^2$] | $V_{OC}$ [mV] | FF [%] | ETA [%] | Sun [mW/cm$^2$] |
|---|---|---|---|---|---|---|
| Ex 14 | 3e | −2.51 | 700 | 66 | 1.2 | 100.00 |
| Ex. 15 | 3i | −4.99 | 780 | 61 | 2.4 | 100.00 |

Example 18

The external quantum efficiency EQE was obtained with an Acton Research Monochromator using additional white background light illumination.

The external quantum efficiency EQE is the ratio of the number of charge carriers collected by the solar cell to the number of photons of a given energy shining on the solar cell from outside (incident photons).

Figure 4:
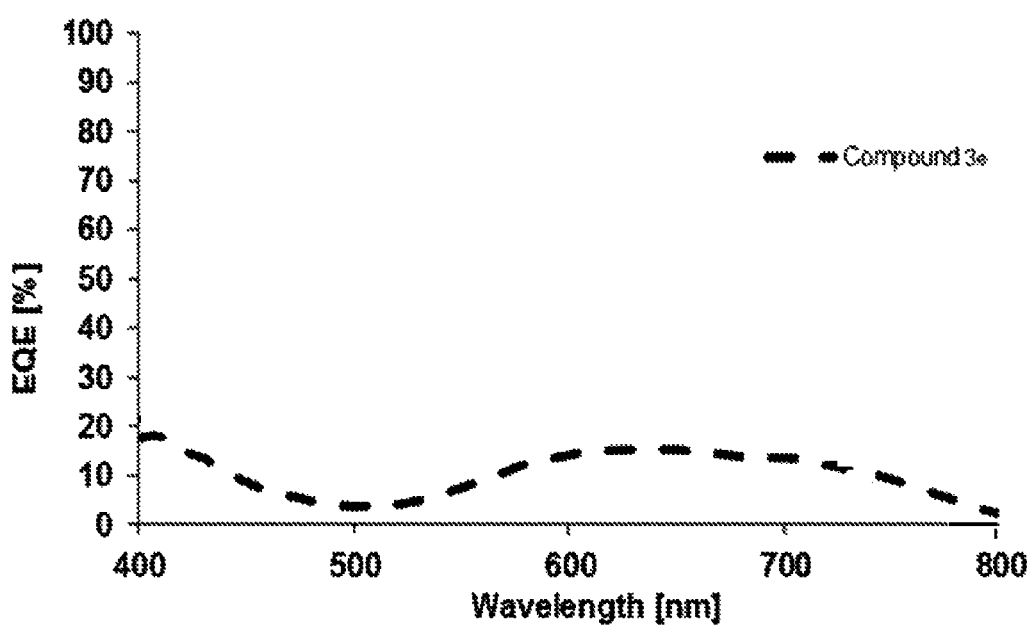
FIG. 4 shows the external quantum efficieny EQE against the wavelength of the solid-state dye-sensitized solar cell (ssDSC) of example 14 comprising the compound of formula 3e.

The plots of the external quantum efficiency EQE against the wavelength of the ssDSC of example 14 is shown in FIG. 4.

Figure 7:
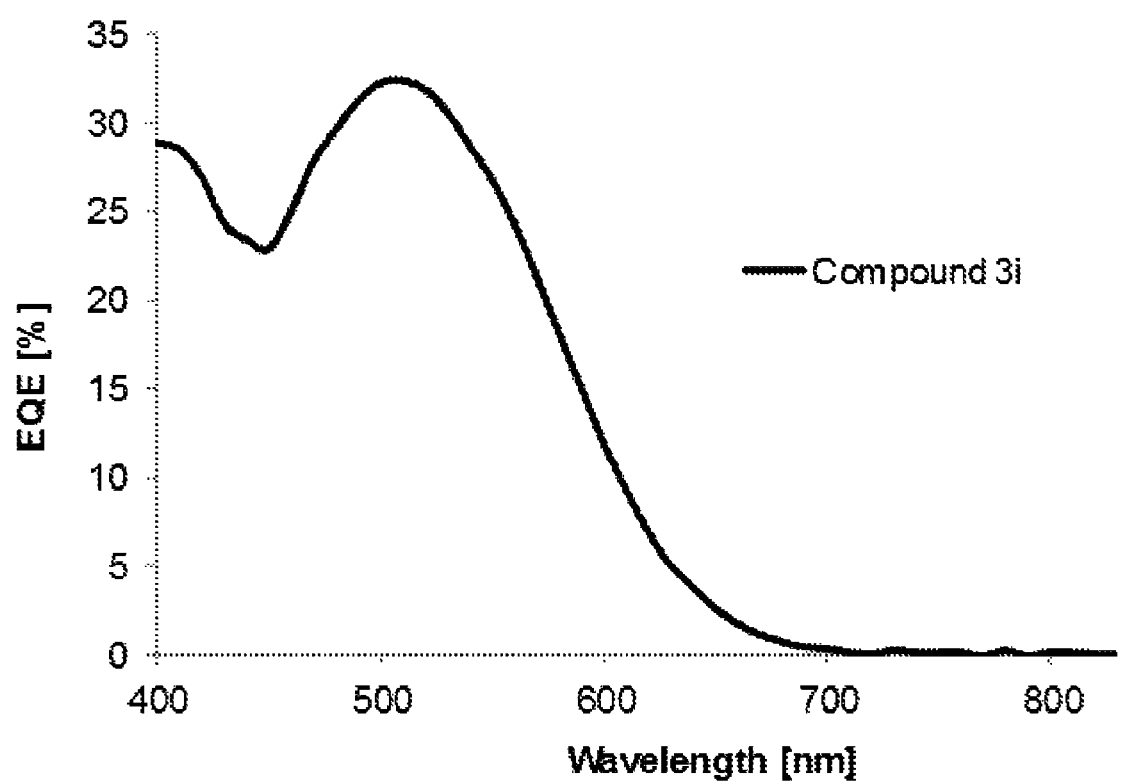
FIG. 7 shows the external quantum efficieny EQE against the wavelength [nm] of the solid-state dye-sensitized solar cell (ssDSC) of example 15 comprising the compound of formula 3i.

The plot of the external quantum efficiency EQE against the wavelength [nm] of the ssDSC of example 15 is shown in FIG. 7.

The invention claimed is:

1. A compound of formula (3)

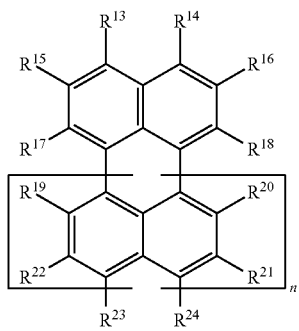

wherein n is 0 or 1, $R^{13}$ and $R^{14}$ are the same or different and are selected from the group consisting of $NHR^{310}$, $NR^{311}R^{312}$, $OR^{313}$, $SR^{314}$ and $R^{315}$, wherein $R^{310}$, $R^{311}$, $R^{312}$, $R^{313}$, $R^{314}$ and $R^{315}$ are $C_{1-20}$-alkyl, $C_{2-20}$-alkenyl, $C_{2-20}$-alkynyl, $C_{5-8}$-cycloalkyl, $C_{6-14}$-aryl or heteroaryl, provided that $R^{315}$ does not represent a methyl group, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3010}R^{3011}$, O—$R^{3012}$ and S—$R^{3013}$, and $C_{6-14}$-aryl and heteroaryl may be substituted with one or more substituents selected from the group consisting of $C_{1-10}$-alkyl, $NR^{3014}R^{3015}$, O—$R^{3016}$ and S—$R^{3017}$, wherein $R^{3010}$, $R^{3011}$, $R^{3012}$, $R^{3013}$, $R^{3014}$, $R^{3015}$, $R^{3016}$ and $R^{3017}$ are the same or different and are $C_{1-10}$-alkyl or phenyl, or $R^{13}$ and $R^{14}$ together are selected from the group consisting of

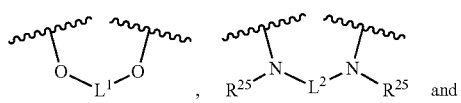

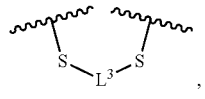

wherein $L^1$ and $L^2$ are $C_{1-6}$-alkylene, $C_{6-14}$-arylene, or $C_{1-6}$-alkylene-$C_{6-14}$-arylene-$C_{1-6}$-alkylene, $R^{25}$ is H, $C_{1-20}$-alkyl, $C_{2-20}$-alkenyl, $C_{2-20}$-alkynyl, $C_{5-8}$-cycloalkyl, $C_{6-14}$-aryl or heteroaryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3030}R^{3031}$, O—$R^{3032}$ and S—$R^{3033}$, and $C_{6-14}$-aryl and heteroaryl may be substituted with one or more substituents selected from the group consisting of $C_{1-10}$-alkyl, $NR^{3034}R^{3035}$, O—$R^{3036}$ and S—$R^{3037}$, wherein $R^{3030}$, $R^{3031}$, $R^{3032}$, $R^{3033}$, $R^{3034}$, $R^{3035}$, $R^{3036}$ and $R^{3037}$ are the same or different and are $C_{1-10}$-alkyl or phenyl, $L^3$ is a direct bond, $C_{1-6}$-alkylene, $C_{6-14}$-arylene, or $C_{1-6}$-alkylene-$C_{6-14}$-arylene-$C_{1-6}$-alkylene, $R^{15}$, $R^{16}$, $R^{17}$, $R^{18}$, $R^{19}$, $R^{20}$, $R^{21}$ and $R^{22}$ are the same or different and are selected from the group consisting of H, F, Cl, Br, I, CN, $R^{300}$, $OR^{301}$, $SR^{302}$, $OC(O)R^{303}$, $C(O)OR^{304}$ and $NR^{305}R^{306}$, wherein $R^{300}$, $R^{301}$, $R^{302}$, $R^{303}$, $R^{304}$, $R^{305}$ and $R^{306}$ are $C_{1-20}$-alkyl, $C_{2-20}$-alkenyl, $C_{2-20}$-alkynyl, $C_{5-8}$-cycloalkyl, $C_{6-14}$-aryl or heteroaryl, wherein $C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3000}R^{3001}$, O—$R^{3002}$, S—$R^{3003}$, $NO_2$, CN and halogen, and $C_{6-14}$-aryl and heteroaryl may be substituted with one or more substituents selected from the group consisting of $C_{1-10}$-alkyl, $NR^{3004}R^{3005}$, O—$R^{3006}$, S—$R^{3007}$, $NO_2$, CN and halogen, wherein $R^{3000}$, $R^{3001}$, $R^{3002}$, $R^{3003}$, $R^{3004}$, $R^{3005}$, $R^{3006}$ and $R^{3007}$ are the same or different and are $C_{1-10}$-alkyl or phenyl, or $R^{17}$ and $R^{19}$, respectively, $R^{18}$ and $R^{20}$ together are

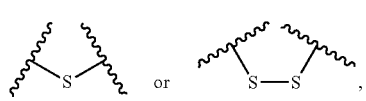

and $R^{23}$ and $R^{24}$ together are

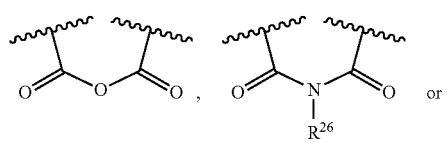

-continued

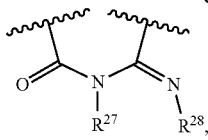

wherein
$R^{26}$, $R^{27}$ and $R^{28}$ are H, $C_{1-20}$-alkyl, $C_{2-20}$-alkenyl, $C_{2-20}$-alkynyl, $C_{5-8}$-cycloalkyl, $C_{6-14}$-aryl or heteroaryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $COOM^1$, $SO_3M^1$, $PO_3M^1$, $NO_2$, CN and halogen, and
$C_{6-14}$-aryl and heteroaryl may be substituted with one or more substituents selected from the group consisting of $C_{1-10}$-alkyl, $COOM^1$, $SO_3M^1$, $PO_3M^1$, $NO_2$, CN and halogen,
wherein $M^1$ is H, alkali metal or $N(R^{3020}R^{3021}R^{3022}R^{3023})$,
wherein $R^{3020}$, $R^{3021}$, $R^{3022}$, and $R^{3023}$ are the same or different and are $C_{1-10}$-alkyl,
or
$R^{27}$ and $R^{28}$ together with the unit

form a five or six membered ring which may be substituted with one or more substituents selected from the group consisting of $COOM^2$, $SO_3M^2$, $PO_3M^2$, $NO_2$, CN and halogen,
wherein $M^2$ is H, alkali metal or $N(R^{3024}R^{3025}R^{3026}R^{3027})$,
wherein $R^{3024}$, $R^{3025}$, $R^{3026}$, and $R^{3027}$ are the same or different and are $C_{1-10}$-alkyl,
with the proviso that if n is 1, $R^{13}$ and $R^{14}$ are phenyl substituted with $N(phenyl)_2$, $R^{15}$, $R^{16}$, $R^{17}$, $R^{18}$, $R^{21}$ and $R^{22}$ are H, one of $R^{19}$ and $R^{20}$ is phenyl substituted with $N(phenyl)_2$, and the other of $R^{19}$ and $R^{20}$ is H or phenyl substituted with $N(phenyl)_2$, then $R^{23}$ and $R^{24}$ together are not

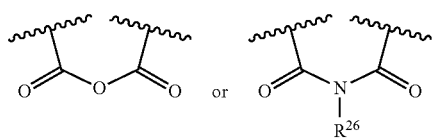

wherein $R^{26}$ is 2-ethylhexyl.

2. The compound of claim 1, wherein n is 1.

3. The compound of claim 2, wherein $R^{15}$, $R^{16}$, $R^{21}$ and $R^{22}$ are H, and $R^{17}$, $R^{18}$, $R^{19}$ and $R^{20}$ are the same or different and are selected from the group consisting of H, F, Cl, Br, I, CN, $R^{300}$, $OR^{301}$, $SR^{302}$, $OC(O)R^{303}$, $C(O)OR^{304}$ and $NR^{305}R^{306}$,
wherein $R^{300}$, $R^{301}$, $R^{302}$, $R^{303}$, $R^{304}$, $R^{305}$ and $R^{306}$ are $C_{1-20}$-alkyl, $C_{2-20}$-alkenyl, $C_{2-20}$-alkynyl, $C_{5-8}$-cycloalkyl or $C_{6-14}$-aryl, wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3000}R^{3001}$, $O-R^{3002}$, $S-R^{3003}$, $NO_2$, CN and halogen, and
$C_{6-14}$-aryl may be substituted with one or more substituents selected from the group consisting of $C_{1-10}$-alkyl, $NR^{3004}R^{3005}$, $O-R^{3006}$, $S-R^{3007}$, $NO_2$, CN and halogen,
wherein $R^{3000}$, $R^{3001}$, $R^{3002}$, $R^{3003}$, $R^{3004}$, $R^{3005}$, $R^{3006}$ and $R^{3007}$ are the same or different and are $C_{1-10}$-alkyl or phenyl,
or
$R^{17}$ and $R^{19}$, respectively, $R^{18}$ and $R^{20}$ together are

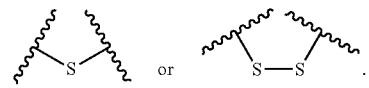

4. The compound of claim 3, wherein $R^{15}$, $R^{16}$, $R^{21}$ and $R^{22}$ are H, and $R^{17}$, $R^{18}$, $R^{19}$ and $R^{20}$ are the same or different and are H or Cl.

5. The compound of claim 1, wherein $R^{13}$ and $R^{14}$ are the same or different and are selected from the group consisting of $NHR^{310}$, $NR^{311}R^{312}$ and $R^{315}$,
wherein
$R^{310}$, $R^{311}$, $R^{312}$ and $R^{315}$ are $C_{1-20}$-alkyl, $C_{2-20}$-alkenyl, $C_{2-20}$-alkynyl, $C_{5-8}$-cycloalkyl or $C_{6-14}$-aryl, provided that $R^{315}$ does not represent a methyl group,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3010}R^{3011}$, $O-R^{3012}$ and $S-R^{3013}$, and
$C_{6-14}$-aryl may be substituted with one or more substituents selected from the group consisting of $C_{1-10}$-alkyl, $NR^{3014}R^{3015}$, $O-R^{3016}$ and $S-R^{3017}$,
wherein $R^{3010}$, $R^{3011}$, $R^{3012}$, $R^{3013}$, $R^{3014}$, $R^{3015}$, $R^{3016}$ and $R^{3017}$ are the same or different and are $C_{1-10}$-alkyl or phenyl,
or
$R^{13}$ and $R^{14}$ together are selected from the group consisting of

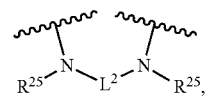

wherein
$L^2$ is $C_{1-6}$-alkylene, $C_{6-14}$-arylene, or $C_{1-6}$-alkylene-$C_{6-14}$-arylene-$C_{1-6}$-alkylene,
$R^{25}$ is H, $C_{1-20}$-alkyl, $C_{2-20}$-alkenyl, $C_{2-20}$-alkynyl, $C_{5-8}$-cycloalkyl, or $C_{6-14}$-aryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3030}R^{3031}$, $O-R^{3032}$ and $S-R^{3033}$, and
$C_{6-14}$-aryl may be substituted with one or more substituents selected from the group consisting of $C_{1-10}$-alkyl, $NR^{3034}R^{3035}$, $O-R^{3036}$ and $S-R^{3037}$, wherein $R^{3030}$, $R^{3031}$, $R^{3032}$, $R^{3033}$, $R^{3034}$, $R^{3035}$, $R^{3036}$ and $R^{3037}$ are the same or different and are $C_{1-10}$-alkyl or phenyl.

6. The compound of claim 1, wherein $R^{13}$ and $R^{14}$ are the same or different and are selected from the group consisting of $NHR^{310}$ and $R^{315}$,
wherein
$R^{310}$ and $R^{315}$ are $C_{6-14}$-aryl,
wherein
$C_{6-14}$-aryl may be substituted with $NR^{3014}R^{3015}$,
wherein $R^{3014}$ and $R^{3015}$ are phenyl,
or
$R^{13}$ and $R^{14}$ together are

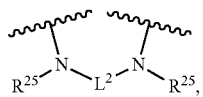

wherein
$L^2$ is $C_{1-6}$-alkylene or $C_{6-14}$-arylene,
$R^{25}$ is H or $C_{6-14}$-aryl.

7. The compound of claim 1, wherein $R^{23}$ and $R^{24}$ together are

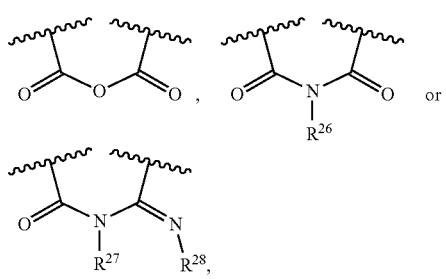

wherein
$R^{26}$, $R^{27}$ and $R^{28}$ are $C_{1-20}$-alkyl or $C_{6-14}$-aryl,
wherein
$C_{1-20}$-alkyl may be substituted with one or more substituents selected from the group consisting of phenyl, $COOM^1$, $SO_3M^1$, $PO_3M^1$, $NO_2$, CN and halogen, and
$C_{6-14}$-aryl may be substituted with one or more substituents selected from the group consisting of $C_{1-10}$-alkyl, $COOM^1$, $SO_3M^1$, $PO_3M^1$, $NO_2$, CN and halogen,
wherein $M^1$ is H, alkali metal or $N(R^{3020}R^{3021}R^{3022}R^{3023})$,
wherein $R^{3020}$, $R^{3021}$, $R^{3022}$, and $R^{3023}$ are the same or different and are $C_{1-10}$-alkyl,
or
$R^{27}$ and $R^{28}$ together with the unit

form a five or six membered ring which may be substituted with one or more substituents selected from the group consisting of $COOM^2$, $SO_3M^2$, $PO_3M^2$, $NO_2$, CN and halogen,
wherein $M^2$ is H, alkali metal or $N(R^{3024}R^{3025}R^{3026}R^{3027})$, wherein $R^{3024}$, $R^{3025}$, $R^{3026}$, and $R^{3027}$ are the same or different and are $C_{1-10}$-alkyl.

8. The compound of claim 1, wherein $R^{23}$ and $R^{24}$ together are

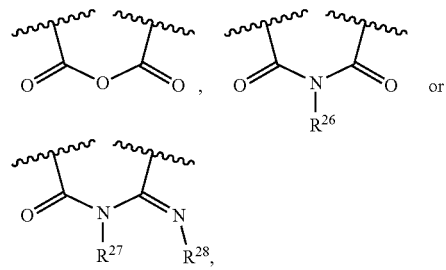

wherein
$R^{26}$, $R^{27}$ and $R^{28}$ are $C_{1-20}$-alkyl or $C_{6-14}$-aryl,
wherein
$C_{1-20}$-alkyl may be substituted with $COOM^1$,
wherein $M^1$ is H,
or
$R^{27}$ and $R^{28}$ together with the unit

form a five membered ring which may be substituted with one or more substituents selected from the group consisting of $COOM^2$ and CN,
wherein $M^2$ is H.

9. A process for the preparation of a compound of formula (3) according to claim 1,

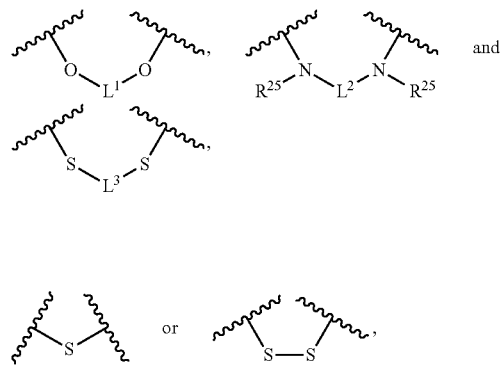

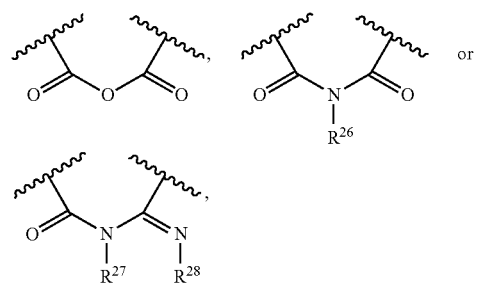

the process comprising treating a compound of formula (2)

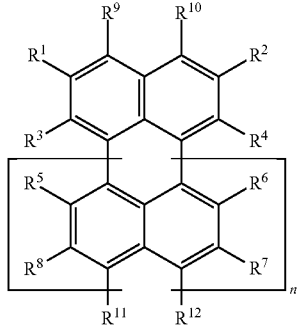

(2)

wherein
n has the meaning as depicted for formula (3),
$R^9$ and $R^{10}$ are the same or different and are COOH or COOR$^{29}$,
wherein $R^{29}$ is $C_{1-20}$-alkyl, $C_{2-20}$-alkenyl, $C_{2-20}$-alkynyl, $C_{5-8}$-cycloalkyl, $C_{6-14}$-aryl or heteroaryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, NR$^{2010}$R$^{2011}$, O—R$^{2012}$ and S—R$^{2013}$, and
$C_{6-14}$-aryl and heteroaryl may be substituted with one or more substituents selected from the group consisting of $C_{1-10}$-alkyl, NR$^{2014}$R$^{2015}$, O—R$^{2016}$ and S—R$^{2017}$,
wherein R$^{2010}$, R$^{2011}$, R$^{2012}$ and R$^{2013}$, R$^{2014}$, R$^{2015}$, R$^{2016}$ and R$^{2017}$ are the same or different and are $C_{1-10}$-alkyl or phenyl,
or
$R^9$ and $R^{10}$ together are

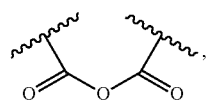 [SMILES: *C(=O)OC(*)=O]

$R^1$, $R^2$, $R^3$, $R^4$, $R^5$, $R^6$, $R^7$ and $R^8$ are the same or different and are selected from the group consisting of H, F, Cl, Br, I, CN, R$^{200}$, OR$^{201}$, SR$^{202}$, OC(O)R$^{203}$, C(O)OR$^{204}$ or NR$^{205}$R$^{206}$,
wherein R$^{200}$, R$^{201}$, R$^{202}$, R$^{203}$, R$^{204}$, R$^{205}$ and R$^{206}$ are $C_{1-20}$-alkyl, $C_{2-20}$-alkenyl, $C_{2-20}$-alkynyl, $C_{5-8}$-cycloalkyl, $C_{6-14}$-aryl or heteroaryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, NR$^{2000}$R$^{2001}$, O—R$^{2002}$, S—R$^{2003}$, NO$_2$, CN and halogen, and
$C_{6-14}$-aryl and heteroaryl may be substituted with one or more substituents selected from the group consisting of $C_{1-10}$-alkyl, NR$^{2004}$R$^{2005}$, O—R$^{2006}$, S—R$^{2007}$, NO$_2$, CN and halogen, wherein R$^{2000}$, R$^{2001}$, R$^{2002}$, R$^{2003}$, R$^{2004}$, R$^{2005}$, R$^{2006}$ and R$^{2007}$ are the same or different and are $C_{1-10}$-alkyl or phenyl,
or
$R^3$ and $R^5$, respectively, $R^4$ and $R^6$ together are

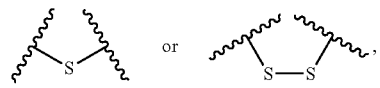

and
$R^{11}$ and $R^{12}$ together are

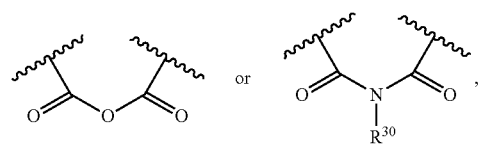

wherein R$^{30}$ is $C_{1-20}$-alkyl, $C_{2-20}$-alkenyl, $C_{2-20}$-alkynyl, $C_{5-8}$-cycloalkyl, $C_{6-14}$-aryl or heteroaryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, NO$_2$, CN and halogen, and
$C_{6-14}$-aryl and heteroaryl may be substituted with one or more substituents selected from the group consisting of $C_{1-10}$-alkyl, NO$_2$, CN and halogen,
with
a) M$^3$OH, wherein M$^3$ is an alkali metal, N(R$^{400}$R$^{401}$R$^{402}$R$^{403}$), P(R$^{400}$R$^{401}$R$^{402}$R$^{403}$) or guanidinium,
wherein R$^{400}$, R$^{401}$, R$^{402}$ and R$^{403}$ are the same or different and are selected from the group consisting of H, $C_{1-20}$-alkyl and $C_{6-14}$-aryl,
wherein
$C_{1-20}$-alkyl may be substituted with phenyl, and
$C_{6-14}$-aryl may be substituted with $C_{1-10}$-alkyl,
b) an acid
and
c) an X-donor, wherein X is Cl, Br or I,
in order to obtain a compound of formula (1)

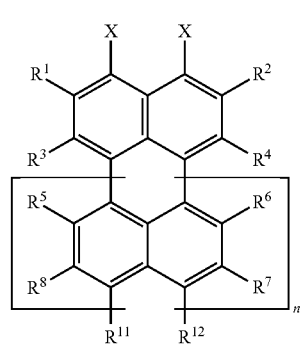

(1)

wherein
n has the meaning as depicted for formula (3),
X has the meaning as depicted for the X-donor, $R^1$, $R^2$, $R^3$, $R^4$, $R^5$, $R^6$, $R^7$, $R^8$, $R^{11}$ and $R^{12}$ have the meaning as depicted for formula (2).

10. The process of claim 9, wherein $R^9$ and $R^{10}$ together are

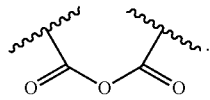 [SMILES: *C(=O)OC(*)=O]

11. The process of claim 9, wherein $R^{11}$ and $R^{12}$ together are

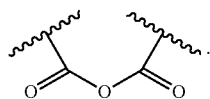 [SMILES: *C(=O)OC(*)=O]

12. The process of claim 9, wherein n is 1.

13. The process of claim 12, wherein $R^1$, $R^2$, $R^7$ and $R^8$ are H, and $R^3$, $R^4$, $R^5$ and $R^6$ are the same or different and are selected from the group consisting of H, F, Cl, Br, I, CN, $R^{200}$, $OR^{201}$, $SR^{202}$, $OC(O)R^{203}$, $C(O)OR^{204}$ or $NR^{205}R^{206}$,
wherein $R^{200}$, $R^{201}$, $R^{202}$, $R^{203}$, $R^{204}$, $R^{205}$ and $R^{206}$ are $C_{1-20}$-alkyl, $C_{2-20}$-alkenyl, $C_{2-20}$-alkynyl, $C_{5-8}$-cycloalkyl or $C_{6-14}$-aryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{2000}R^{2001}$, $O-R^{2002}$, $S-R^{2003}$, $NO_2$, CN and halogen, and
$C_{6-14}$-aryl may be substituted with one or more substituents selected from the group consisting of $C_{1-10}$-alkyl, $NR^{2004}R^{2005}$, $O-R^{2006}$, $S-R^{2007}$, $NO_2$, CN and halogen,
wherein $R^{2000}$, $R^{2001}$, $R^{2002}$, $R^{2003}$, $R^{2004}$, $R^{2005}$, $R^{2006}$ and $R^{2007}$ are the same or different and are $C_{1-10}$-alkyl or phenyl,
or
$R^3$ and $R^5$, respectively, $R^4$ and $R^6$ together are

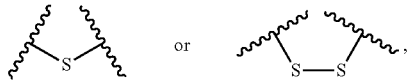

and
$R^{15}$, $R^{16}$, $R^{21}$ and $R^{22}$ are H, and $R^{17}$, $R^{18}$, $R^{19}$ and $R^{20}$ are the same or different and are selected from the group consisting of H, F, Cl, Br, I, CN, $R^{300}$, $OR^{301}$, $SR^{302}$, $OC(O)R^{303}$, $C(O)OR^{304}$ and $NR^{305}R^{306}$,
wherein $R^{300}$, $R^{301}$, $R^{302}$, $R^{303}$, $R^{304}$, $R^{305}$ and $R^{306}$ are $C_{1-20}$-alkyl, $C_{2-20}$-alkenyl, $C_{2-20}$-alkynyl, $C_{5-8}$-cycloalkyl or $C_{6-14}$-aryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3000}R^{3001}$, $O-R^{3002}$, $S-R^{3003}$, $NO_2$, CN and halogen, and
$C_{6-14}$-aryl may be substituted with one or more substituents selected from the group consisting of $C_{1-10}$-alkyl, $NR^{3004}R^{3005}$, $O-R^{3006}$, $S-R^{3007}$, $NO_2$, CN and halogen, wherein $R^{3000}$, $R^{3001}$, $R^{3002}$, $R^{3003}$, $R^{3004}$, $R^{3005}$, $R^{3006}$ and $R^{3007}$ are the same or different and are $C_{1-10}$-alkyl or phenyl,
or
$R^{17}$ and $R^{19}$, respectively, $R^{18}$ and $R^{20}$ together are

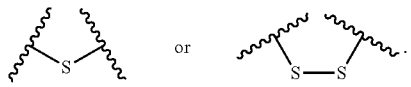

14. The process of claim 13, wherein $R^1$, $R^2$, $R^7$ and $R^8$ are H, and $R^3$, $R^4$, $R^5$ and $R^6$ are the same or different and are H or Cl, and $R^{15}$, $R^{16}$, $R^{21}$ and $R^{22}$ are H, and $R^{17}$, $R^{18}$, $R^{19}$ and $R^{20}$ are the same or different and are H or Cl.

15. The process of claim 9, wherein $R^{13}$ and $R^{14}$ are the same and are selected from the group consisting of $NHR^{310}$, $NR^{311}R^{312}$ and $R^{315}$,
wherein
$R^{310}$, $R^{311}$, $R^{312}$ and $R^{315}$ are $C_{1-20}$-alkyl, $C_{2-20}$-alkenyl, $C_{2-20}$-alkynyl, $C_{5-8}$-cycloalkyl or $C_{6-14}$-aryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3010}R^{3011}$, $O-R^{3012}$ and $S-R^{3013}$, and
$C_{6-14}$-aryl may be substituted with one or more substituents selected from the group consisting of $C_{1-10}$-alkyl, $NR^{3014}R^{3015}$, $O-R^{3016}$ and $S-R^{3017}$,
wherein $R^{3010}$, $R^{3011}$, $R^{3012}$, $R^{3013}$, $R^{3014}$, $R^{3015}$, $R^{3016}$ and $R^{3017}$ are the same or different and are $C_{1-10}$-alkyl or phenyl,
or
$R^{13}$ and $R^{14}$ together are

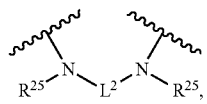

wherein
$L^2$ is $C_{1-6}$-alkylene, $C_{6-14}$-arylene, or $C_{1-6}$-alkylene-$C_{6-14}$-arylene-$C_{1-6}$-alkylene,
$R^{25}$ is H, $C_{1-20}$-alkyl, $C_{2-20}$-alkenyl, $C_{2-20}$-alkynyl, $C_{5-8}$-cycloalkyl, or $C_{6-14}$-aryl,
wherein
$C_{1-20}$-alkyl, $C_{2-20}$-alkenyl, $C_{2-20}$-alkynyl and $C_{5-8}$-cycloalkyl may be substituted with one or more substituents selected from the group consisting of phenyl, $NR^{3030}R^{3031}$, $O-R^{3032}$ and $S-R^{3033}$, and
$C_{6-14}$-aryl may be substituted with one or more substituents selected from the group consisting of $C_{1-10}$-alkyl, $NR^{3034}R^{3035}$, $O-R^{3036}$ and $S-R^{3037}$,
wherein $R^{3030}$, $R^{3031}$, $R^{3032}$, $R^{3033}$, $R^{3034}$, $R^{3035}$, $R^{3036}$ and $R^{3037}$ are the same or different and are $C_{1-10}$-alkyl or phenyl.

16. The process of claim 9, wherein $R^{13}$ and $R^{14}$ are the same and are selected from the group consisting of $NHR^{310}$ and $R^{315}$,
wherein
$R^{310}$ and $R^{315}$ are $C_{6-14}$-aryl,
wherein
$C_{6-14}$-aryl may be substituted with $NR^{3014}R^{3015}$,
wherein $R^{3014}$ and $R^{3015}$ are phenyl,
or
$R^{13}$ and $R^{14}$ together are

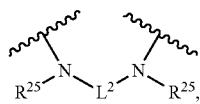

wherein $L^2$ is $C_{1-6}$-alkylene or $C_{6-14}$-arylene, $R^{25}$ is H or $C_{6-14}$-aryl.

17. The process of claim 9, wherein $R^{23}$ and $R^{24}$ together are

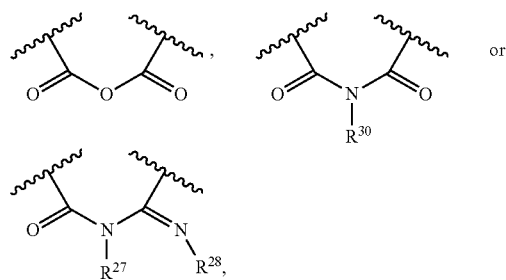

wherein $R^{26}$, $R^{27}$ and $R^{28}$ are $C_{1-20}$-alkyl or $C_{6-14}$-aryl, wherein $C_{1-20}$-alkyl may be substituted with one or more substituents selected from the group consisting of phenyl, $COOM^1$, $SO_3M^1$, $PO_3M^1$, $NO_2$, CN and halogen, and $C_{6-14}$-aryl may be substituted with one or more substituents selected from the group consisting of $C_{1-10}$-alkyl, $COOM^1$, $SO_3M^1$, $PO_3M^1$, $NO_2$, CN and halogen, wherein $M^1$ is H, alkali metal or $N(R^{3020}R^{3021}R^{3022}R^{3023})$, wherein $R^{3020}$, $R^{3021}$, $R^{3022}$, and $R^{3023}$ are the same or different and are $C_{1-10}$-alkyl, or $R^{27}$ and $R^{28}$ together with the unit

form a five or six membered ring which may be substituted with one or more substituents selected from the group consisting of $COOM^2$, $SO_3M^2$, $PO_3M^2$, $NO_2$, CN and halogen, wherein $M^2$ is H, alkali metal or $N(R^{3024}R^{3025}R^{3026}R^{3027})$, wherein $R^{3024}$, $R^{3025}$, $R^{3026}$, and $R^{3027}$ are the same or different and are $C_{1-10}$-alkyl.

18. The process of claim 9, wherein $R^{23}$ and $R^{24}$ together are

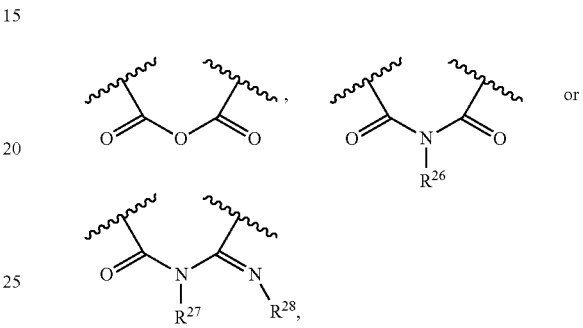

wherein $R^{26}$, $R^{27}$ and $R^{28}$ are $C_{1-20}$-alkyl or $C_{6-14}$-aryl, wherein $C_{1-20}$-alkyl may be substituted with $COOM^1$, wherein $M^1$ is H, or $R^{27}$ and $R^{28}$ together with the unit

form a five membered ring which may be substituted with one or more substituents selected from the group consisting of $COOM^2$ and CN, wherein $M^2$ is H.

* * * * *